United States Patent
Jones et al.

(10) Patent No.: US 12,337,315 B2
(45) Date of Patent: *Jun. 24, 2025

(54) AUTOMATED MICROSCOPIC CELL ANALYSIS

(71) Applicant: Medica Corporation, Bedford, MA (US)

(72) Inventors: Ronald Jones, Newton, NH (US); Adrian Gropper, Watertown, MA (US); Robert Hagopian, Belmont, MA (US); Charles Rogers, Halifax, MA (US); Thomas Vitella, Sandown, NH (US); Tyler Cote, Chelmsford, MA (US); Donald Barry, Groton, MA (US); Dirk Osterloh, Unna (DE); Chen Yi, Boxborough, MA (US)

(73) Assignee: Medica Corporation, Bedford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/114,754

(22) Filed: Feb. 27, 2023

(65) Prior Publication Data

US 2024/0024866 A1    Jan. 25, 2024

Related U.S. Application Data

(63) Continuation of application No. 16/803,897, filed on Feb. 27, 2020, now Pat. No. 11,590,496, which is a
(Continued)

(51) Int. Cl.
*G01N 15/14* (2024.01)
*B01L 3/00* (2006.01)
(Continued)

(52) U.S. Cl.
CPC ... *B01L 3/502715* (2013.01); *B01L 3/502738* (2013.01); *G01N 15/1434* (2013.01);
(Continued)

(58) Field of Classification Search
CPC .... G01N 33/48; G01N 33/49; G01N 33/4915; G01N 33/50; G01N 33/5002;
(Continued)

(56) References Cited

U.S. PATENT DOCUMENTS 5,812,419 A    9/1998   Chupp
9,767,343 B1 *  9/2017   Jones .................. G01N 15/1434
(Continued)

FOREIGN PATENT DOCUMENTS

WO    2011130629    10/2011

OTHER PUBLICATIONS

European Pat. Apl. No. EP3482189; Intention to Grant, dated Mar. 26, 2024.
(Continued)

*Primary Examiner* — Maureen Wallenhorst
(74) *Attorney, Agent, or Firm* — Kristofer E. Elbing

(57) ABSTRACT

This disclosure describes single-use test cartridges, cell analyzer apparatus, and methods for automatically performing microscopic cell analysis tasks, such as counting and analyzing blood cells in biological samples. A small measured quantity of a biological sample, such as whole blood, is placed in a mixing bowl on the disposable test cartridge after being inserted into the cell analyzer. The analyzer also deposits a known amount of diluent/stain in the mixing bowl and mixes it with the blood. The analyzer takes a measured amount of the mixture and dispenses in a sample cup on the cartridge in fluid communication with an imaging chamber. The geometry of the imaging chamber is chosen to maintain the uniformity of the mixture, and to prevent cells from
(Continued)

crowding or clumping as it is transferred into the imaging chamber by the analyzer. Images of all of the cellular components within the imaging chamber are counted and analyzed to obtain a complete blood count.

12 Claims, 21 Drawing Sheets

Related U.S. Application Data continuation of application No. 15/616,327, filed on Jun. 7, 2017, now Pat. No. 10,625,259, which is a continuation-in-part of application No. 15/221,285, filed on Jul. 27, 2016, now Pat. No. 9,767,343, which is a continuation of application No. 15/017,498, filed on Feb. 5, 2016, now Pat. No. 11,478,789, which is a continuation-in-part of application No. 14/947,971, filed on Nov. 20, 2015, now abandoned.

(60) Provisional application No. 62/394,702, filed on Sep. 14, 2016, provisional application No. 62/360,236, filed on Jul. 8, 2016, provisional application No. 62/138,359, filed on Mar. 25, 2015, provisional application No. 62/113,360, filed on Feb. 6, 2015, provisional application No. 62/084,760, filed on Nov. 26, 2014.

(51) Int. Cl.
*G01N 15/10* (2024.01)
*G01N 15/1434* (2024.01)
*G01N 21/05* (2006.01)
*G01N 33/487* (2006.01)
*G01N 33/49* (2006.01)
*G01N 33/50* (2006.01)
*G01N 33/80* (2006.01)
*G06V 20/69* (2022.01)
*G01N 1/10* (2006.01)
*G01N 1/30* (2006.01)

(52) U.S. Cl.
CPC .......... *G06V 20/693* (2022.01); *G06V 20/698* (2022.01); *B01L 2200/027* (2013.01); *B01L 2200/0605* (2013.01); *B01L 2200/0647* (2013.01); *B01L 2200/16* (2013.01); *B01L 2300/0627* (2013.01); *B01L 2400/0633* (2013.01); *B01L 2400/0644* (2013.01); *G01N 1/10* (2013.01); *G01N 1/30* (2013.01); *G01N 2015/1006* (2013.01); *G01N 2015/1486* (2013.01); *G01N 21/05* (2013.01); *G01N 33/487* (2013.01); *G01N 33/49* (2013.01); *G01N 33/4915* (2013.01); *G01N 33/5094* (2013.01); *G01N 33/80* (2013.01)

(58) Field of Classification Search
CPC ...... G01N 33/5094; G01N 33/80; G01N 1/10; G01N 1/30; G01N 21/05; G01N 2015/0065; G01N 2015/0073; G01N 2015/0076; G01N 2015/008; G01N 2015/0084; G01N 2015/1006; G01N 2015/1486; G01N 15/1434; G01N 15/1463; G01N 15/1484; G01N 2035/00148; Y10T 436/10; Y10T 436/101666; Y10T 436/107497; Y10T 436/108331; Y10T 436/25; Y10T 436/2575; G06K 9/00134; G06K 9/00147; B01L 2200/027; B01L 2200/0605; B01L 2200/0647; B01L 2200/16; B01L 2300/0627; B01L 2400/0633; B01L 2400/0644; B01L 3/502715; B01L 3/502738; G06V 20/693; G06V 20/698
USPC .. 436/8, 10, 17, 18, 63, 164, 165, 174, 179, 436/180; 435/29, 39, 287.1, 287.3, 435/288.7; 422/403, 404, 82.05, 82.09, 422/501–505, 507, 509, 554
See application file for complete search history.

(56) References Cited

U.S. PATENT DOCUMENTS

| | | | |
|---|---|---|---|
| 10,625,259 B1 * | 4/2020 | Jones | ................ B01L 3/502761 |
| 11,478,789 B2 * | 10/2022 | Jones | ................ B01L 3/502738 |
| 11,480,778 B2 * | 10/2022 | Jones | ....................... G01N 1/38 |
| 11,590,496 B2 * | 2/2023 | Jones | ................ G01N 33/56972 |
| 11,921,104 B2 | 3/2024 | Barry et al. | |
| 2008/0003142 A1 | 1/2008 | Link | |
| 2009/0269799 A1 * | 10/2009 | Winkelman | ....... G01N 35/1016 435/29 |
| 2010/0291588 A1 | 11/2010 | McDevitt | |
| 2014/0273064 A1 | 9/2014 | Smith | |
| 2015/0192518 A1 * | 7/2015 | Baxter | ................. G01N 33/585 506/30 |
| 2018/0007319 A1 | 1/2018 | Winkelman | |
| 2021/0231552 A1 | 7/2021 | Kim | |
| 2023/0185070 A1 | 6/2023 | Jones et al. | |
| 2023/0294089 A1 | 9/2023 | Jones et al. | |

OTHER PUBLICATIONS

European Pat. Apl. No. EP3482189; Amendment, dated Oct. 5, 2023.
Japanese Pat. Apl. No. JP2023108204; Office Action, dated Apr. 12, 2024.
Japanese Pat. Apl. No. JP2023108204; Search Report, dated Mar. 12, 2024.
Japanese Pat. Apl. No. JP2019520938; Decision to Grant, dated Jun. 14, 2023.
Japanese Pat. Apl. No. JP2019520938; Written Opinion, dated Apr. 12, 2023.
Japanese Pat. Apl. No. JP2019520938; Record of Communication, dated Apr. 11, 2023.
Japanese Pat. Apl. No. JP2019520938; Office Action, dated Jan. 5, 2023.
U.S. Appl. No. 17/972,458; Office Action, dated Feb. 13, 2024.
U.S. Appl. No. 17/359,733; Notice of Allowance, dated Sep. 14, 2023.
U.S. Appl. No. 17/359,733; Amendment, dated Apr. 6, 2023.
U.S. Appl. No. 16/235,099; Notice of Allowance, dated May 25, 2023.
U.S. Appl. No. 16/235,099; Amendment, dated Dec. 15, 2022.
Grossi et al., A Portable Sensor with Disposable Electrodes for Water Quality Assessment, IEEE, Feb. 25, 2016.

* cited by examiner

| Description | Bright-field | Fluorescent |
|---|---|---|
| Lymphocyte |  |  |
| Monocyte |  |  |
| Neutrophil |  |  |
| Eosinophil |  |  |
| Basophil |  |  |
| Nucleated Red Blood Cell |  |  |

AUTOMATED MICROSCOPIC CELL ANALYSIS

CROSS-REFERENCE TO RELATED APPLICATIONS

This application is a continuation of U.S. application Ser. No. 16/803,897, filed Feb. 27, 2020, now U.S. Pat. No. 11,590,496, which is a continuation of U.S. application Ser. No. 15/616,327, now U.S. Pat. No. 10,625,259, filed Jun. 7, 2017, which claims priority to U.S. provisional application No. 62/394,702, filed Sep. 14, 2016, and to U.S. provisional application No. 62/360,236, filed Jul. 8, 2016, and which is a continuation-in-part of U.S. application Ser. No. 15/221,285, now U.S. Pat. No. 9,767,343, filed Jul. 27, 2016, which is a continuation of U.S. application Ser. No. 15/017,498, now U.S. Pat. No. 11,478,789, filed Feb. 5, 2016, which is a continuation-in-part of U.S. application Ser. No. 14/947,971, filed Nov. 20, 2015, now abandoned, which claims priority to U.S. provisional applications Nos. 62/138,359, filed Mar. 25, 2015, 62/113,360 filed Feb. 6, 2015, and 62/084,760, filed Nov. 26, 2014. All of the above-listed applications are herein incorporated by reference.

FIELD OF THE INVENTION

This invention pertains to analyzers and methods for automatically performing microscopic cell analysis tasks, such as counting blood cells in biological samples. More specifically, the present disclosure relates to single use devices, apparatus and methods used to count red blood cells, white blood cells and platelets, and measurements related to these particles.

BACKGROUND OF THE INVENTION

There are a variety of methods for enumerating particles, such as blood cells, in a biological sample. Determining the number of cells per unit volume in a sample provides the physician important diagnostic information. The most elementary method of counting cells consists of introducing a diluted biological sample into a hemocytometer and examining it with a microscope. A hemocytometer is a device with an optically clear chamber having a known depth, typically 100 microns, and ruled markings to define a unit volume, typically 0.01 µL. A uniform mixture of diluted whole blood, for example, may be introduced into the hemocytometer by capillary action to form a monolayer. Using a microscope to visualize the diluted sample, cells of different types can be counted manually in a limited number of marked areas. Counts are aggregated to compute the number of cells per unit volume. This manual method is time consuming, tedious, and requires a skilled technician to operate the microscope and to recognize the various types of cells, and is prone to error. Its accuracy is limited by the number of cells counted and the uniformity of the monolayer formed by introduction of the diluted sample.

Consequently, automated methods, such as impedancemetry (Coulter principle U.S. Pat. No. 2,656,508) and flow cytometry, have been developed for rapid counting, sizing, and classification of a relatively large number of cells for diagnostic tests such as the Complete Blood Count (CBC), sometimes referred to a CBC with a five part differential. These automated methods also have shortcomings. The analyzers are relatively large and expensive and require skilled operators for their use and maintenance. Such analyzers are typically available only in centralized laboratories. Blood samples are collected in special containers having an anticoagulant to keep the blood from clotting while being transported to the lab. This process adds costs and risk of erroneous results from transport, handling, labeling and transcription, as well as a time delay in obtaining the results. These analyzers also flag or reject in excess of 20% of the tested samples for further review by a manual differential. Only highly skilled technicians can perform a manual differential. A flag is commonly generated by impedance or flow cytometry counters because the impedance or scatter profiles of a population of cells are ambiguous. Microscopic imaging analysis is not susceptible to the same ambiguities as impedancemetry and flow cytometry, and thus is used as a reference method. Similarly, automated imaging analysis have a much lower flag rate.

The CBC generally includes measures of white blood cells (leukocytes) per unit volume (WBC), red blood cells (erythrocytes) per unit volume (RBC), platelets (thrombocytes) per unit volume (PLT), hematocrit (HCT) or packed cell volume (PCV), hemoglobin (HGB), and measurements related to red cells including mean corpuscular volume (MCV), mean corpuscular hemoglobin (MCH), mean corpuscular hemoglobin content (MCHC), and red cell distribution width (RDW). A diagnostic test sometimes referred to as a "CBC with differential", or "CBC with five part diff", will also include neutrophil granulocytes (NEU), Lymphocytes (LYM), Monocytes (MON), Eosinophil granulocytes (EO) and Basophil granulocytes (BASO) per unit volume or as a percentage of the white blood cells (WBC). The CBC with differential also may include counts of Immature Cells (IC), atypical lymphocytes, nucleated Red Blood Cells (nRBC), and Reticulocytes (RETIC) per unit volume of the blood sample.

The CBC provides a panel of blood cell measurements that can be used to diagnose a wide variety of abnormal conditions, such as anemia or infection, or to monitor a patient's treatment, such as chemotherapy. Because of its usefulness, the CBC analysis is one of the most commonly performed diagnostic tests in medicine, but patients typically wait a day or more for results. If microscopic cell analysis could be performed in a portable, easy-to-use, analyzer close to the patient, results could have a more immediate impact in improving patient care. A simple system able to provide the CBC in the physician's office, or at bedside, or in the Critical Care Unit (CCU) or Intensive Care Unit (ICU), or in the hospital emergency room within a few minutes and using a drop of blood from a finger-stick, could have enormous impact on the delivery and affordability of health care.

Recent patent documents have described simpler devices than centralized lab hematology analyzers for performing cell analysis of blood samples. In U.S. Pat. No. 7,771,658, issued to Larsen, the applicant, provides technology for performing a flow-cell analysis of blood cells in a single use disposable cartridge. Larsen describes means for taking an exact amount of blood sample, diluting the amount of blood with a precise volume of diluent, and mixing the blood with the diluent to obtain a homogeneous solution. Larsen utilizes a single use cartridge to flow a measured amount of the mixture of sample and diluent through an orifice at a rate of several thousand particles per second, and counts, sizes, and classifies the particles for analysis in accordance with the Coulter principle. Because Larsen's disclosure is directed to the analysis of a small sample of whole blood, errors in metering various volumes or in the mixing or sampling steps can significantly impact the accuracy of the results.

PCT Patent Number WO 2014099629 issued to Ozcan et al. describes a system for analyzing a blood sample with a mobile electronic device having a camera. The sample preparation process for each test requires accurate measurement of 10 μL, of whole blood to be mixed with 85 μL, phosphate buffered saline and 5 μL of nucleic acid stain. Ten (10) μL of this diluted mixed sample are then loaded into a cell counting chamber with precise channel height of 100 μm and are imaged by a digital camera. A separate cell counting chamber is needed for analysis of red cells, white cells, and hemoglobin, and each test should be performed separately. Accuracy of the final result is not only dependent on the accurate measurements of the various sample preparation steps, including the precise metering of the sample and diluent, but also on the precise fabrication of the counting chambers. Maintaining uniformity and consistency of the 100 μm dimension of the channel height in a disposable cartridge is difficult to achieve in a low cost device.

U.S. Pat. No. 8,837,803 to Wang et al. describes a method for determining cell volume of red blood cells, which seeks to avoid the errors associated with diluting, mixing, and sampling, by analyzing a sample of substantially undiluted whole blood. In theory this approach has appeal, but the handling of undiluted whole blood is challenging. The cells are so numerous (for example 5,000,000 red cells in 1 that their distribution can be impacted by contact with the surfaces of a disposable cartridge. Additionally, in order to image cells in this overcrowded environment, the imaging chamber should have a depth of only a few microns to prevent the overlapping of cells, and it should be fabricated accurately, because it determines the volume of the blood sample being analyzed.

Therefore a compact, accurate method of performing microscopic cell analysis using digital camera imaging of a diluted sample, which does not require accurate measurement of the diluent volume, or require accurate or precise dimensions of an imaging chamber, is highly desirable.

SUMMARY OF THE INVENTION

An objective of the present invention is to provide an apparatus that can provide counts of cells or other particles of a biological sample per unit volume without requiring an operator having specialized knowledge or specialized skills. Another objective of the present invention is to provide an easy-to-use analyzer that can perform all of the measurements of the CBC in a few minutes. Another object of the invention is to provide an analyzer to perform a CBC on a small finger stick sample. Another objective of the present invention is to provide a method for determining the concentration of particles in a diluted biological sample that does not require accurate measurement of a volume of diluent or reagent mixed with the sample. Another objective of the present invention is to provide ready-to-use reagents and diluent for use in performing the microscopic analysis of a biological sample that do not require preparation, mixing or measurement by the user. Another object of the invention is to create a substantially homogenous monolayer of cells of a diluted sample in a single use disposable device and to perform a CBC analysis in a few minutes. Another objective is to provide a sample collection device that can easily be operated by a user to obtain a biological sample for analysis. Yet another objective is to provide all of the fluidic components of a CBC analyzer in a single-use device, so as to prevent cross contamination between samples and to avoid the need for cleaning and washing of fluidic components of an analyzer. Another objective of the present invention is to provide internal monitoring of the critical process steps of counting cells, so that a potentially erroneous result can be flagged. Still another objective is to provide a method of performing the CBC on a sample immediately after collecting it, and to eliminate transport of the sample to a laboratory or storage of the sample. Some or all of these and/or other objectives or advantages may be accomplished by embodiments of the invention as provided for in the appended claims.

A further object of the invention is to provide a hematology analyzer that performs a CBC using imaging technology instead of the Coulter principle of flow cytometry. Another object of the invention is to provide a hematology analyzer that utilizes a single use disposable imaging chamber. Another object of the invention is to provide a substantially homogenous monolayer of cells and platelets of diluted whole blood in their unrestrained state incontradistiction to cells smeared or sprayed on a glass slide, wherein the cells are mechanically deformed or distorted or flattened, or cells that are sprayed or deposited on a glass slide and fixed. Another object of the invention is to provide an imaging based hematology analyzer that flags samples at a lower rate than hematology analyzers that use impedancemetry or flow cytometry.

The disclosure provides improved methods, systems, and devices for performing counts and measurements of particles in a biological sample. Aspects of the disclosure are directed to determining the concentration of one or more types of particles of a biological sample and providing the result as the number of such particles per unit volume in a few minutes. The particles may be any mass suspended in a liquid that can be recognized by optical inspection using an automated microscope and image analysis techniques well known in the art. Examples of particles include, but are not limited to, blood cells, platelets, sperm, bacteria, spores, and inorganic particles.

While embodiments of the present invention can be used in many applications to count particles suspended in a liquid, the present disclosure will demonstrate benefits of the invention in performing the Complete Blood Count (CBC) or CBC with differential on human or animal blood samples as defined above. The present disclosure describes a single-use test cartridge for use with an apparatus that includes an automated microscope for analyzing cells in a biological sample. The test cartridge is used to collect a biological sample. For example the user can prick the finger of a patient and obtain a whole blood sample and collect the resulting drop of blood in the test cartridge. The user can accomplish this by holding the test cartridge beneath the hanging drop from the patient's finger and then bringing it closer until the drop contacts an input port or sample cup on the test cartridge. In an alternate embodiment, the user may take a blood sample intravenously and transfer it to the test cartridge using a plastic bulb pipette. In one example the single-use test cartridge includes an input port adapted to accept a variety of sources of biological samples including a direct sample, capillary tube, or transfer pipette. In another example, the test cartridge could draw a sample into it by capillary action. The test cartridge may also include a closure that the user applies to cover the input port after the sample has been collected into the test cartridge. The closure may be part of the test cartridge or a separate device. The user may apply the closure manually or the apparatus may automatically move the closure to cover the input port when the test cartridge is docked to the apparatus. The closure provides a physical barrier to avoid subsequent contact with any excess sample on the surface of the test cartridge. The closure has a vent to provide an air path to the input port to allow the liquid sample to move within the test cartridge if a vacuum is applied, as will be described below.

Within the test cartridge, the input port is connected by an input channel to a metering chamber capable of precisely separating a small volume of the sample from the unmeasured sample. As an example, the collected sample volume may be 5-20 μL, of which the metering chamber separates out or isolates 0.1-5 μL for measurement. If a finger stick sample is utilized, a sample volume less than 10 μL, will minimize the risk of hemolysis and the risk of dilution by interstitial fluids. The metering chamber can be a section of a fluid channel, a cavity, or a pass-through conduit within a valve, or another volumetric shape that can be reproducibly fabricated to contain a predetermined volume of the biological sample in the range of 0.1 to 5 μL. Injection molding, compression molding, etching or other processes known to those skilled in the making of lab-on-a-chip or microfluidic devices can be utilized to manufacture the metering chamber.

In one example, the metering chamber is combined with a rotary valve structure by molding a pass-through conduit in the cylindrical stem of the rotary valve. As an example a pass-through conduit having a cylindrical cross section with 0.5 mm diameter and a length of 5 mm, has an internal volume of approximately 1 μL. The pass-through conduit is initially filled with the biological sample by providing a fluid communication path between the input port and input channel, the pass-through conduit, and a vacuum channel. A vacuum applied to the vacuum channel pulls the sample into the pass-through conduit. Alternatively the biological sample can be pulled into the pass-through conduit by capillary action. Once the biological sample has completely filled the pass-through conduit, the cylindrical stem of the rotary valve is rotated until the pass-through conduit is no longer connected to the input channel or the vacuum channel, thus separating or isolating the sample volume contained in the pass-through conduit. Alternatively, a rotary face seal valve, a slide valve, or a fixed volume in the test cartridge could be used to isolate a small volume of the sample.

Further, elements of the test cartridge include a prepackaged liquid reagent or alternatively, a chamber for storing a liquid reagent, together with a mixing chamber, an imaging chamber, and fluid channels through which the sample and liquid reagent may be moved. In one example, after the biological sample has filled the pass-through conduit, the rotary valve is positioned so that the pass-through conduit is placed in fluid communication with both a liquid reagent and the mixing chamber. Empirical studies have determined that a volume of liquid reagent or diluent or stain (referred to hereafter as "diluent/reagent") that is in excess of 3-times the volume of the pass-through conduit is sufficient to wash out the entire isolated sample. In one example, the diluent/reagent is a combination of diluent and stain and is supplied in a volume to provide a dilution ratio of about 40:1. Therefore forty times the volume of the metering chamber can be used to push the isolated sample out of the pass-through conduit and into the mixing chamber, where the sample is uniformly mixed with the diluent/reagent, and then transferred into the imaging chamber.

The single use test cartridge contains an imaging chamber, through which an automated microscope can acquire images of cells in the mixture of diluent/reagent and sample. In one embodiment of the present invention, the isolated sample volume is diluted with a known volume of diluent/reagent, whereby the dilution ratio is established. The volume of the diluent/reagent may be determined by measuring it, for example, by monitoring its flow in a fluid channel of known dimensions with a camera or other fluid sensor such as optical reflective/transmitted or ultrasonic, or by temporarily metering it into a known volume chamber and then using only that known volume for sample dilution. According to this embodiment, the cells in a known volume of the diluted sample are counted, and because the dilution ratio is known, the cell counts per unit volume of the blood sample can be determined. The volume of the diluted sample can be determined by filling an imaging chamber of known volume with the diluted sample. The volume of the imaging chamber may be known by using highly reproducible manufacturing processes, or by measuring each test cartridge at time of manufacture and encoding sizing parameters in the package labeling. Alternatively, a measured amount of the diluted sample can be transferred into an imaging chamber of unknown volume and all the cells in the chamber are counted. A measured amount of the diluted sample can be determined by monitoring its flow from the mixing chamber into a fluid channel of known dimensions by a camera, and isolating a segment. The segment, in turn, is moved into the imaging chamber.

In a preferred embodiment, the isolated sample volume is transferred to the mixing chamber and then to the imaging chamber. According to this embodiment, neither the dilution ratio nor the volume of the diluent needs to be known. The size of the imaging chamber is chosen to ensure that the entire volume of the isolated sample and the diluent/reagent can be contained within the imaging chamber, but the exact dimensions or volume of the chamber do not need to be known. The depth of the imaging chamber should be small enough to prevent the cells from overlapping at the chosen dilution ratio when the cells settle to the bottom. This depth is preferably between about 10 μm and 200 μm. In one embodiment, the depth of the imaging chamber is 100 μm and the ratio of the diluent/reagent to the isolated sample is 40 to 1. The width of the imaging chamber is chosen to provide uniform filling by the different cell sizes and smooth flow without forming voids or crowding of cells. The length of the imaging chamber is calculated based on the depth and width parameters to provide the volume needed to accommodate the entire isolated sample at the chosen dilution ratio, and to provide a safety margin. The shape of the imaging chamber may further be chosen to match the field of view of the digital camera or to facilitate capture of multiple images or to maintain a uniform distribution of cells.

We have found that if the shape of the imaging chamber is square or rectangular having a ratio of length to width of 2:1, the cells will not uniformly fill the imaging chamber. If the mixture of sample and diluent/reagent is uniform when it enters the imaging chamber, the cells will tend to bunch and crowd, particularly near the sides or edges, and when they settle, the layer on the bottom of the imaging chamber will not be homogenous. It is important to obtain a substantially homogenous monolayer of cells in the imaging chamber, as this facilitates the counting of all the cells. We have found that if the width and depth of the imaging chamber are small compared to the length, the cells remain substantially uniformly distributed. Desirably, the length-to-width ratio of the imaging chamber is greater than 10:1. In various embodiments of the present invention, the shape of an imaging chamber may be serpentine, helical, or castellated according to the form factor of the test cartridge. In all of these cases the width and depth are small compared to the length so that the cells due not aggregate on the sides or corners of the imaging chamber, and the layer of cells settling to the bottom of the imaging chamber is substantially homogenous. Those skilled in the art will recognize that other geometries for the imaging chamber, which maintain the distribution of cells when the mixed solution of sample and diluent/reagent is transferred into the imaging chamber may also be utilized.

The design goal of the imaging chamber is to contain all the cells from the original metered chamber and the diluent/reagent in a uniform manner and without significant cell overlap when the cells settle to the bottom of the imaging chamber. The dilution ratio combined with the depth of the imaging chamber can be chosen to minimize the overlapping. As an illustrative example, an imaging chamber may have a width between 0.5 mm and 2.5 mm, a depth from 10 to 200 µm, and the dilution ratio may be from 10:1 to 100:1.

Materials, which contact the cells outside of the imaging chamber, may be chosen to have surface properties to minimize cell adherence. Liquid reagents, which may include a surfactant or cell sphering agent to facilitate cell analysis, may also advantageously minimize red cells being lost during transfer or being overlapped in the imaging chamber. The volume of liquid reagent and the flow velocity may also be chosen to improve the likelihood of transferring every cell from the metering or mixing chamber to the imaging chamber and insuring that the distribution of the cells remains uniform. Yeh-Chan Ahn describes the complex convective diffusion phenomena that is created in a serpentine microchannel which has a varying curvature (See Investigation of laminar dispersion with optical coherence tomography and optical Doppler tomography, Yeh-Chan Ahn, Woonggyu Jung, Jun Zhang, and Zhongping Chen, OPTICS EXPRESS 8164, Vol. 13, No. 20, 3 Oct. 2005). Particles, or in our case, cells which are in suspension and moving through such a microchannel tend to segregate according to their size, density, channel shape and flow velocity. Secondary flow from the serpentine geometry can create vortices as the channel curves causing the cells to be re-mixed into the center of the flow at certain fill velocities. This re-mixing helps maintain a near uniform distribution of the cells as the fluid fills the microchannel. In one embodiment, we have found that a serpentine path that is 1.25 mm wide with turning inside diameter of 1.25 mm and an outside diameter of 2.5 mm, a depth of 0.125 mm, a length of 500 mm, and an effective fill speed of about 24 µL/s insures that the flow of cells remains uniform.

It should be noted that the time to count every cell is directly related to the volume of the metered chamber, and that this creates a trade-off in overall performance. Manufacturing highly reproducible metering chambers is challenging for very small volumes. However, while it may be easier and more reproducible to manufacture a metering chamber with a 5 µL volume than one with a 1 µL volume, it would potentially take five times longer to count every cell, and analyze them, in a 5 uL volume of sample than a 1 uL sample volume. Embodiments of the present invention can provide a solution to this dilemma. By ensuring that the sample and diluent/reagent are well mixed and that a proper dilution ratio is chosen, and by utilizing a serpentine shaped imaging chamber where the length is large compared to the width and depth, the pattern of cells across the imaging chamber is relatively uniform and reproducible. Under these conditions, the layer of cells settling to the bottom of the imaging chamber will be a substantially homogenous monolayer. As a result, instead of imaging the entire layer and counting every cell, one can take representative images or frames that are statistically derived to accurately account for every cell. Thus, within the allowable error for the final result(s), every cell is included in the analysis, whether by actual image or by statistical representation. As an illustrative example, the camera may take up to 20,000 images at 20× in order to scan the entire imaging chamber. Alternatively, every tenth frame could be taken to obtain a statistical representation. Another option would be to divide the imaging chamber into segments and count the cells in every other segment or every third segment and so on. Another alternative to decrease the imaging time would be to scan the entire imaging chamber at 10×/0.25 numerical aperture (NA) or 4×/0.1NA to obtain the total WBC and RBC total counts, and then take images at higher power (20×0.04NA or higher) to obtain the higher-resolution detail needed for counting platelets, reticulocytes, and performing the WBC differential.

Embodiments of the present invention can achieve accurate results independent of the many factors that have impacted the accuracy of results in the prior art. For example, the volume of the diluent/reagent and the dilution ratio do not impact the results, so long as all the cells from the metered sample volume are transferred to the imaging chamber and are not overlapping or crowded, and presented for analysis. Similarly the representativeness of a selected portion of the mixture of sample and reagent, and the homogeneity of the portion, which directly affect the accuracy of results by prior art methods, need have no impact on embodiments of the present invention. Most importantly, the depth and uniformity of the imaging chamber, which has been difficult or expensive to control in other prior art efforts, need not impact the accuracy of results according to embodiments of the present invention.

The present disclosure further describes a cell analyzer that is small and easy to use. The cell analyzer accepts the test cartridge and carries out all the steps of the cell analysis without further input from the user. In one embodiment, the test cartridge contains all diluents and reagents needed to perform a CBC analysis of the patient sample placed in it. In this embodiment, the cell analyzer has fluid handling components including positive and negative pressure sources that interface with the test cartridge when it is placed into the analyzer. One or more connections are made between the analyzer and the cartridge to place these pressure sources into fluid communication with channels in the cartridge to provide a motive force to move liquids within the cartridge. The cell analyzer also has a mechanical valve driver for operating a valve in the test cartridge for controlling the movements of fluids in the test cartridge. When the test cartridge is placed in the analyzer, the mechanical valve driver is connected to a valve indexer to provide means for operating the valve in the test cartridge. The cell analyzer includes a mechanism for release of the diluent/reagent that are stored on board the test cartridge. The cell analyzer further includes fluid control logic to automatically control movement of the fluids in the test cartridge by activating the positive and negative pressure or displacement sources and operating the mechanical valve driver according to pre-programmed sequences. The cell analyzer may include a process monitoring camera positioned to acquire digital images of the movement of fluids in the cartridge. Information from the process monitoring camera can be used to provide feedback for the fluid control logic or for monitoring critical steps.

The present disclosure also provides devices and methods for managing and/or monitoring the sample collection and preparation process to ensure accurate results. In applications where the present invention is used to perform a CBC analysis, if too much time lapses between obtaining the blood sample and completing sample dilution and staining within the test cartridge, the blood may clot or the cells may settle resulting in erroneous results. In one embodiment of the present invention that mitigates this risk, the test cartridge is placed on the analyzer in a slide-out tray which initiates process monitoring within the analyzer. The blood sample is added to the cartridge by dispensing a free-hanging drop, or by using a capillary tube that is inserted into the test cartridge or by transferring a sample and depositing it with a pipette. Immediately after the sample has been added to the cartridge, the user presses "Run Sample" to initiate the test sequence. Because the cartridge is controlled by the analyzer, the time to collect the sample is known and can be short enough to avoid the need for anticoagulant coating or mixing the blood sample.

In an alternate embodiment that allows the sample to be collected several minutes before processing, an anticoagulant, such as K2 or K3 EDTA, is provided. This may be achieved by coating the sample input cup with anticoagulant, by use of a capillary tube coated with anticoagulant for a finger-stick sample, or by sampling from an evacuated blood collection tube such as a Becton Dickenson Vacutainer® containing anticoagulant. To manage cell settling, the test cartridge according to this embodiment has a timing indicator which is initiated when the input port is opened or the blood sample is introduced. The timing indicator can be a color-changing chemical reaction, a time delayed thermal reaction, an analog or digital timer, or other means known in the art. When the user loads the test cartridge into the analyzer, the timing indicator is read and if needed, the sample is mixed before proceeding. If too much time has lapsed the sample can be rejected to avoid producing erroneous results.

In yet another embodiment that facilitates remote sample collection, the test cartridge is docked to a carrier system. The carrier system is a handheld or portable device used to facilitate a portion, or all, of the sample preparation steps. After blood is added to the test cartridge using any of the above mentioned methods, the carrier system according to this embodiment draws the blood into the cartridge, meters the sample, performs quality checks, and completes the sample preparation to present the cells for image analysis. The carrier system would then either eject the test cartridge for the user to transfer to the imaging analyzer, or the carrier system could be docked to the imaging analyzer for an automated handoff. In this embodiment anticoagulant coatings are not needed and there is no risk of cell settling because the critical steps are initiated as soon as the sample is placed in the test cartridge.

Combinations of the workflow devices and methods are also contemplated in the present disclosure. By way of example, a simple carrier system could incorporate a digital timer and a mechanism able to meter the sample, but not perform quality checks or full sample preparation. These additional steps would be done by the cell analyzer.

The cell analyzer contains an automated microscope including an objective lens, focusing mechanism, brightfield and/or fluorescent light sources or both, filters, a dichroic mirror and a digital camera. In some embodiments, the cell analyzer may further include an illumination source and photometric detector for measuring light transmission at one or multiple wavelengths for measuring the concentration of an analyte in the sample. For example, the test cartridge can include a photometric chamber which is in fluid communication with the input port by means of a fluidic channel, and through which the sample can be transferred for photometric analysis, such as a hemoglobin measurement.

By way of example, to measure hemoglobin, the cell analyzer may have an illumination source consisting of two light emitting diodes (LEDs) providing excitation at wavelengths of 502 nm and 880 nm. The light path for the LEDs and a photometric detector are approximately 0.030" diameter. The 502 nm LED may be selected for absorbance measurement because of an isobestic point of oxyhemoglobin (O2Hb) and deoxyhemoglobin (RHb). Also at 502 nm, the slope of the O2Hb and RHb curves are very low, resulting in minimal variation with varying oxygen saturation (sO2) levels. Furthermore, the carboxyhemoglobin (COHb) curve is also close to this isobestic point, resulting in very little effect from COHb. An 880 nm LED can measure the background scatter effects caused by RBCs, WBCs, lipids, etc. This is particularly important when taking measurements on whole blood. This measurement may also be performed on lysed blood, with or without a reagent for converting the hemoglobin to a single form, such as reduced hemoglobin, methemoglobin, azidemethemoglobin or cyanomethemogloin. In the case of a conversion to a single form of hemoglobin, a different peak wavelength for absorption measurement may be used, such as 540 nm or 555 nm.

Disclosed and contemplated aspects also include an example of a test cartridge that is not preloaded with reagents, and instead, is coupled to a reagent supply module contained on board the cell analyzer. The user loads the reagent supply module into the cell analyzer where it is utilized for multiple test cartridges. When the reagent supply module is exhausted or expires, the cell analyzer alerts the user and will not perform additional tests until the reagent supply module is exchanged. The reagent supply module includes a cradle for receiving the test cartridge, a vessel for holding a liquid diluent/reagent, a diluent delivery pump in fluid communication with the vessel, and a diluent/reagent output port constructed to interface with the test cartridge when the cartridge is in the cradle. In one example the size of the vessel is of sufficient capacity to provide diluent/reagents to dilute several samples (50-100) with a reagent to sample ratio of 10:1 to about 250:1. The diluent/reagent supply module may include a self-priming mechanism for priming the liquid reagent and eliminating air bubbles. 'The reagent supply module may further include a chamber for collecting waste diluent/reagent from the priming process.

In another embodiment contemplated in the present disclosure, a small measured volume of whole blood may be mixed manually with an imprecise amount of diluent/reagent in a sample preparation device. For instance, the known volume of sample and imprecise diluent/reagent may be put into a sample tube and gently rocked back and forth a few times. The entire mixed volume is then transferred by using a transfer pipette or similar device to a test cartridge having an imaging chamber sufficiently large to contain the entire mixed volume. According to embodiments of the present invention, if all of the cells in the imaging chamber are counted (either directly or by statistical sampling), then the concentration of cells per unit volume can be determined, without one needing to know the volume of the diluent/reagent, the dilution ratio, or the volume of the mixed sample in the imaging chamber, or the volume of the imaging chamber occupied by the mixture. One drawback to this embodiment is the practical difficulty in measuring a small volume of sample, e.g. 1 uL. If a large volume of sample is chosen, such as 10 uL, it will take a longer time to count all the cells and it will require a relatively large imaging chamber. In the case of a 10 uL sample size and a dilution ratio of 50:1, an imaging chamber of 500 uL would be required. An alternative embodiment would be to take a 10 uL sample and mix it with a precise volume of diluent, and then taking a portion of the mixture and transferring it into an imaging chamber sufficiently large to contain the portion of mixture. If every cell of the mixture is counted, the number of cells per unit volume can be easily determined, since the dilution ratio is known.

Diluent/reagents that are preloaded in the test cartridge, or are provided in a separate sample preparation device, or by a supply module are in a ready-to-use format. For a CBC analysis, the reagents may include a membrane-permeable dye, such as Acridine Orange to differentially stain the DNA and RNA of cells in whole blood. Other stains known to those skilled in the art, such as cyanine dyes, can also be used to stain the blood cells. In an alternative arrangement, the stain may be provided in a dry reagent form together with a diluent that is mixed with the dry reagent as needed. Multiple stains can be included in a combination reagent. In one embodiment, the reagents may include an antibody conjugated to a detectable label that targets specific cells or specific antigens associated with cells. The detectable label may be a dye, a fluorescent dye, quantum dot, colloidal metal such as gold, silver, or platinum or other detectable constructs known in the art. The detectable label can also be used to detect a cell-specific antibody, such as CD3, CD4, CD14, CD16, CD19, CD34, CD45, CD56, or any other of the enumerated Cluster of Differentiation markers. The detectable label can also be used to detect bacterial or parasitic pathogens, platelets, recirculating tumor cells, leukemic cells, stem cells or any combination of these.

In other embodiments the liquid reagent may contain a surfactant such as polysorbate or sodium dodecyl sulfate (SDS), an anticoagulant such as EDTA, and/or a sphering agent such a zwitterionic detergent to provide isovolumetric reshaping of the red blood cells to facilitate cell size measurement and computation of the mean corpuscular volume (MCV).

Systems according to the invention can exhibit better quantitative accuracy than manual microscope analyses using a manual hemocytomer or similar device, which tend to be limited by variability in sample preparation and limited counting statistics. In embodiments of the present invention, sample preparation is improved by removing critical operator fluid handling steps and by automation of all dilution steps. Because every cell and platelet is counted in the entire metered volume of sample, any error in the sample dilution is irrelevant.

Systems according to the invention can also save time that would otherwise be allocated to manual hemocytometer slide preparation, setup time, and microscope focusing, which can limit the number of blood samples that can be analyzed. Automation can greatly increase the rate of image acquisition and analysis, allowing for more cells to be analyzed and counted. This can improve the counting statistics and overall precision of the system.

Systems according to the invention can also extend the capabilities of cell counting methods by enabling CBC point-of-care testing, i.e. near patient testing, to permit immediate clinical decisions to be made. Personnel having a relatively low skill level can operate the systems. The analyzers can be engineered to be inexpensively manufactured and easily serviced, allowing them to be more readily deployed at point-of-care sites, such as at the patient's bedside, in physician's offices, and at emergency sites.

BRIEF DESCRIPTION OF THE DRAWINGS

In the drawings, like reference characters generally refer to the same parts throughout the different views. The drawings are not necessarily to scale, emphasis instead being placed upon illustrating the principles of the invention. In the following description, various embodiments of the present invention are described with reference to the following drawings, in which.

DETAILED DESCRIPTION

Figure 1:
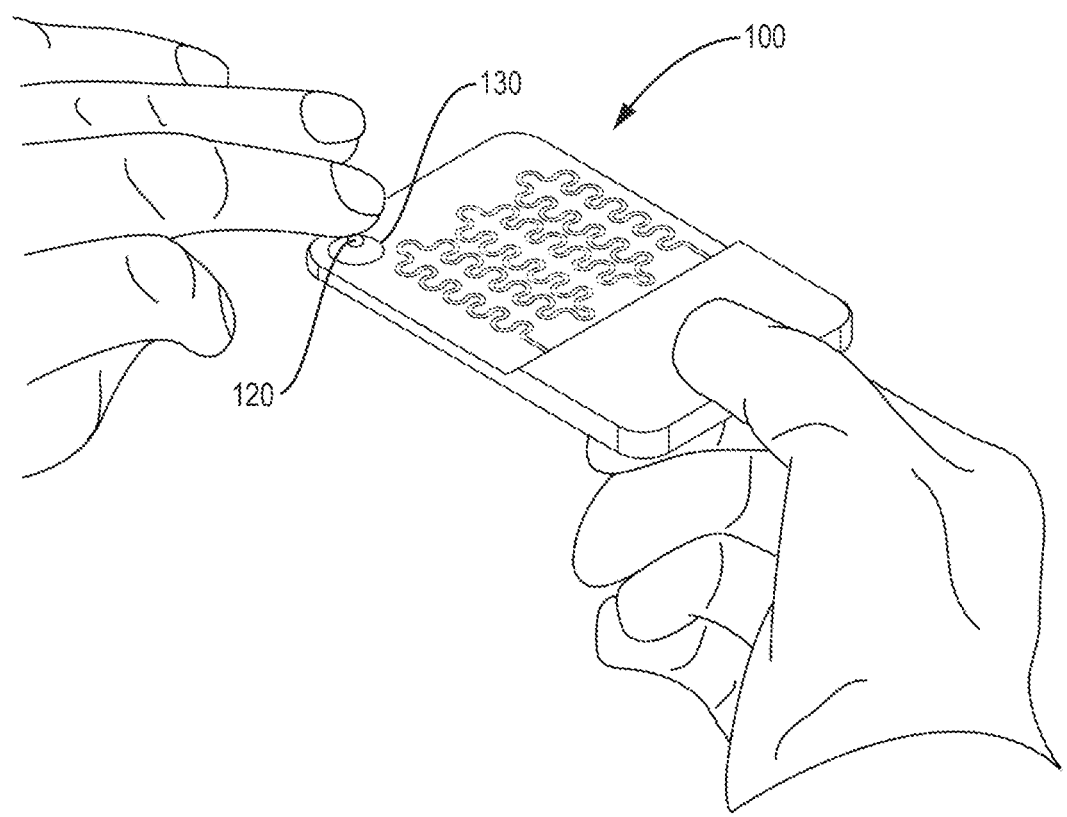
FIG. 1 is a perspective view of an illustrative test cartridge being positioned to collect a drop of blood from a patient's finger.

FIG. 1 illustrates test cartridge 100 being positioned to collect a drop of blood 120 from a patient's finger. The test cartridge is held beneath the hanging drop 120, so that it contacts the input port 130 of the test cartridge 100. The input port 130 comprises a recessed area or opening that may be coated with an anticoagulant and have surface treatment or features such as small columns to increase surface retention to collect and hold the blood sample. In an alternate embodiment, the blood sample 120 may be collected intravenously and introduced to input port 130 by a transfer pipette or capillary tube. The transfer pipette or capillary may contain an anticoagulant coating according to the desired workflow. The volume of blood or other biological sample placed in input port 130 is sufficient to visually fill the recessed sample area, but is unmeasured.

Figure 2A:
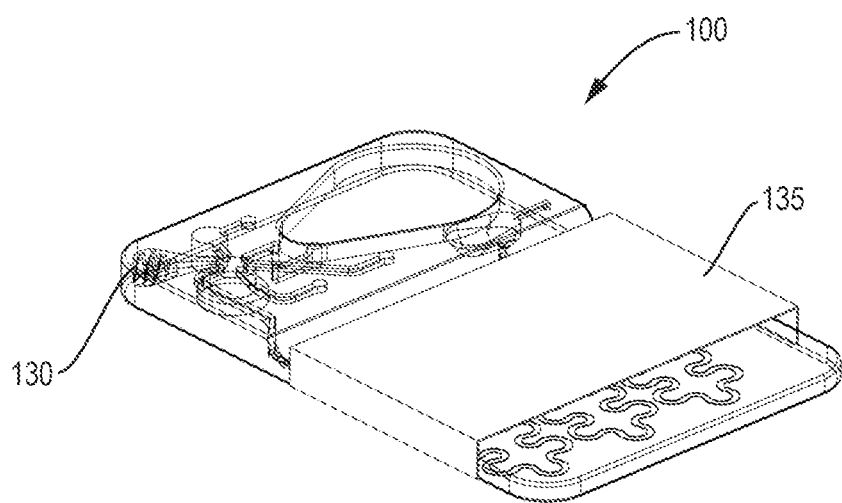
FIG. 2A is a perspective view of an illustrative test cartridge with a cover shown in the open position to receive a biological sample.
Figure 2B:
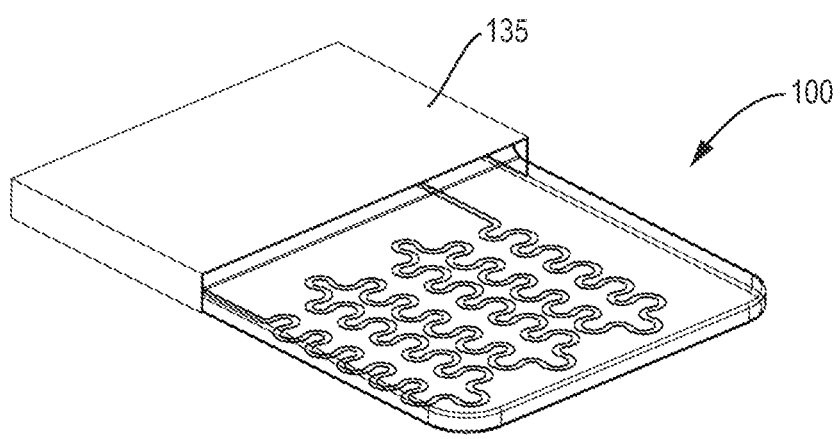
FIG. 2B is a perspective view of the test cartridge shown in FIG. 2A with the cover shown in the closed position ready for analysis.
Figure 3:
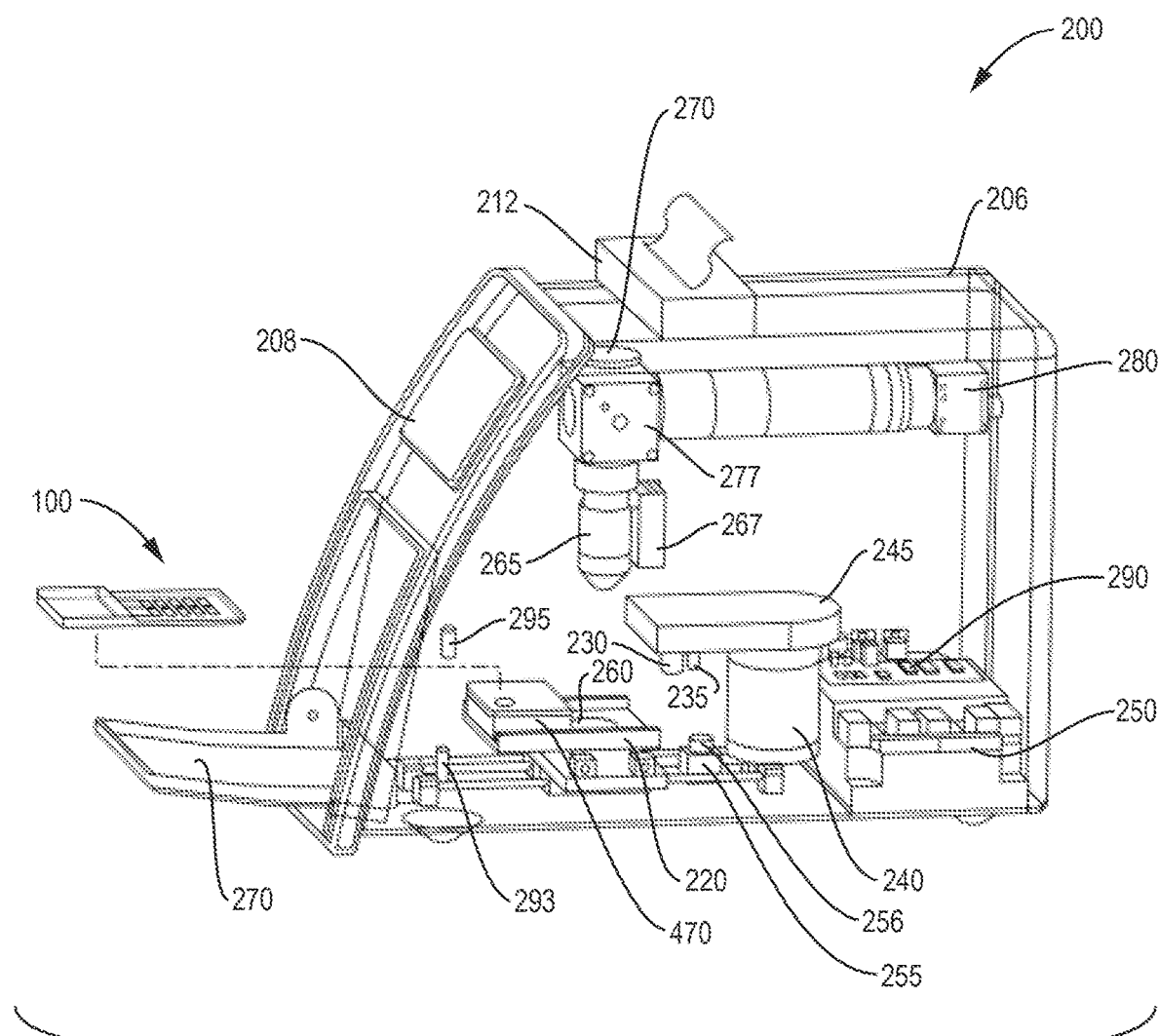
FIG. 3 is a cut-away view of an illustrative cell analyzer showing internal components with a test cartridge being inserted.

FIG. 2A shows test cartridge 100 with closure 135 shown in the open position to provide access to input port 130. Closure 135 is adapted to slide relative to the test cartridge 100 and may have detent or other positioning features that facilitate placing it in different positions. After the biological sample has been collected into input port 130, closure 135 may be moved to the position shown in FIG. 2B to cover the input port 130. The closure 135 may be moved by the user prior to inserting it into the analyzer as shown in FIG. 3. Alternatively, closure 135 may be moved by an operation within the cell analyzer. Alternate embodiments of closure 135 may include graphics, identifying information, or instructions to the user. While the closure 135 is illustrated as a sliding component, other means of closing the input port 130 are contemplated including a cap that hinges upward, a small surface cover that swivels away from and returns to cover the input port 130, or an adhesive component that sticks to the input port 130 or area surrounding it. In all cases the closure 135 includes a vent or air path to the input port to allow the blood sample to move into the test cartridge 100.

FIG. 3 is a cut-away view of an illustrative cell analyzer 200 with test cartridge 100 positioned so that the operator can introduce it into the analyzer. From the outside of the cell analyzer 200, one can see the housing 206, a user-interface screen 208, a printer 212, and a cartridge loading door 217. When the cartridge loading door 217 is opened, the test cartridge 100 can be placed on a cradle 220 of x-y stage 225, configured to receive test cartridge 100 from the user. The cradle 220 provides mechanical alignment of the cartridge to facilitate connections that are made between the analyzer and the cartridge. For example, a mechanical presser foot 230 may be placed in contact with a flexible surface on the test cartridge to provide mechanical pressure onto packaged, on-board reagents. Some embodiments of the cell analyzer 200 may utilize a reagent supply module 470 as further described with reference to FIG. 6. Reagent supply module 470 may be installed on x-y stage 225 and has a receiving area 473 (see FIG. 6) to provide alignment of the test cartridge 402 with the reagent module 470.

A valve driver 235 can be positioned to operate a rotary valve on the test cartridge. A vacuum/pressure pump 240 supplies negative or positive pressure to a manifold 245, which interfaces with the test cartridge 100 when it is placed in the cell analyzer as described below. The cell analyzer 200 further includes system controller 250 to control movement of the fluids in the test cartridge by activating the vacuum/pressure pump 240, moving the mechanical presser foot 230, or operating the valve driver 235 according to pre-programmed sequences. Monitoring camera 255, positioned to acquire digital images of the fluids in the cartridge, provides feedback for the system controller 250. Monitoring light source 256 may be a ring illuminator that surrounds the lens of the monitoring camera 255. Information from the monitoring camera 255 is used to provide feedback for controlling movement of liquids, for positioning the rotary valve, and for confirming critical steps.

Also shown in FIG. 3 are the components that comprise the automated microscope of the cell analyzer 200. At the base of the analyzer, bright-field light source 260 provides illumination through the test cartridge to the objective lens 265, operatively coupled to focusing mechanism 267. At the top of the analyzer, fluorescent light source 270 provides illumination through dichroic mirror 277 to provide fluorescent excitation of the sample. At the rear of the analyzer, digital camera 280 captures images of the test cartridge 100 and transmits them to image processor/computer 290. In some embodiments, the cell analyzer may further include a photometric light source 293 and photometric detector 295 for measuring light transmission at one or multiple wavelengths in a chamber in test cartridge 100, such as for measuring hemoglobin, as is more fully explained below.

Figure 4:
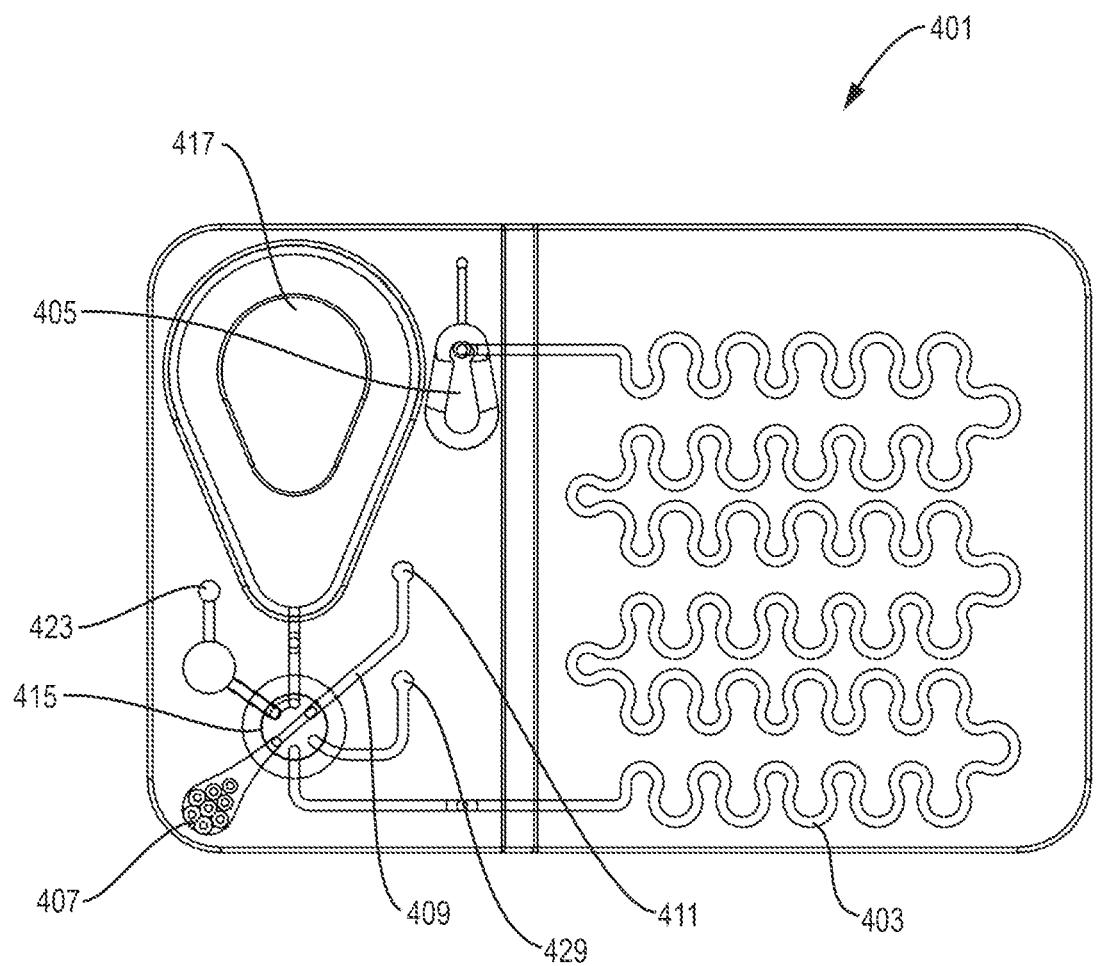
FIG. 4 is a plan view of an illustrative test cartridge of the type that includes reagents for conducting a test.

FIG. 4 shows an illustrative test cartridge 401 of the type that includes liquid reagents stored in a blister pack 417 for conducting a test. The test cartridge 401 has an input port 407 for receiving a sample, a passive mixing chamber 405 for mixing the sample with diluent/reagent, and an imaging chamber 403 for capturing images of the cells in the mixture of sample and diluent/reagent for analysis. In this embodiment, photometric chamber 409 may be filled with whole blood to make optical absorbance measurements to determine concentrations of certain analytes in the sample, such as hemoglobin. A rotary valve 415 provides fluidic connections between various fluidic channels, vents, and ports, including sample driver port 411, vent 423 and mixture driver port 429 as will be described in FIGS. 8A-8F.

Figure 5:
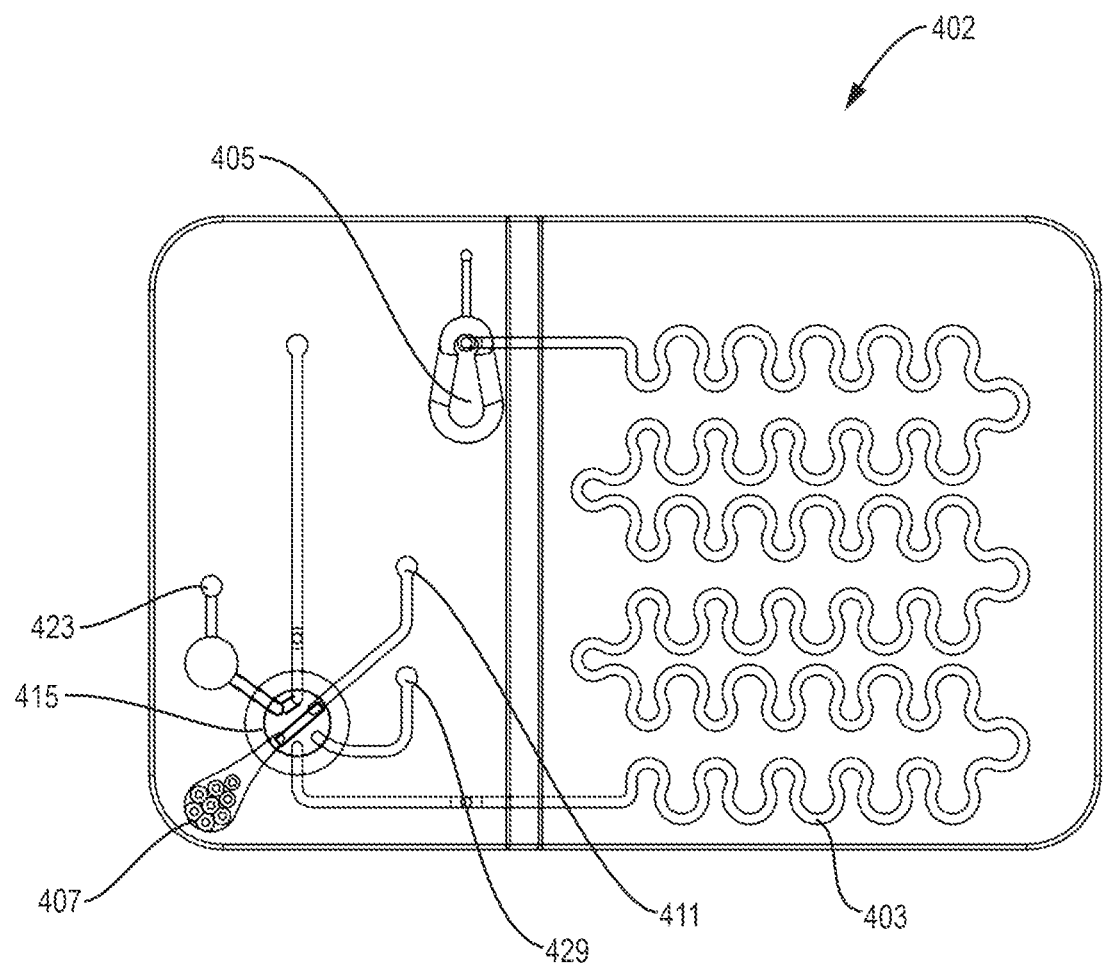
FIG. 5 is a plan view of an illustrative test cartridge of the type that does not include reagents.

FIG. 5 shows an illustrative test cartridge 402 of the type that does not include on-board diluent/reagents. Many of the functional components are identical to those illustrated with reference to test cartridge 401, but instead of on-board diluent/reagents, test cartridge 402 has a reagent input port 460 adapted to be connected to an external source of diluent/reagent. Test cartridge 402 may be used in embodiments in which diluent/reagents that are needed for an analysis may be too costly to package individually or may require refrigerated storage. In such an embodiment, diluent/reagent may be provided from a source within cell analyzer 200 or from a reagent supply module.

Figure 6:
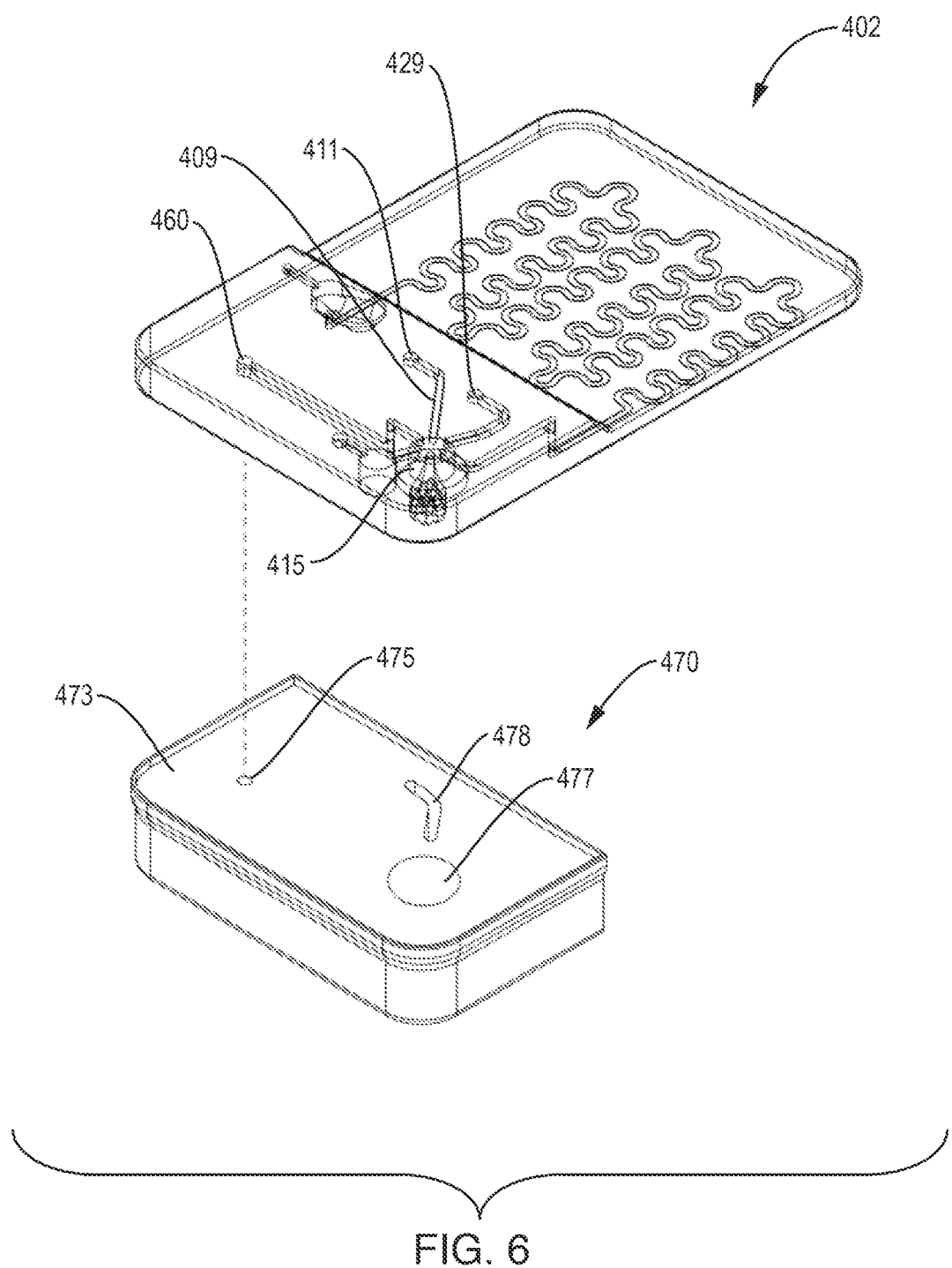
FIG. 6 is a perspective view of an illustrative reagent supply module showing a test cartridge ready to be joined with the module.

FIG. 6 shows an illustrative reagent supply module 470 positioned to receive test cartridge 402. The reagent supply module 470 includes a receiving area 473 for docking the test cartridge 402, and contains a vessel for holding the diluent/reagent, a reagent metering pump adapted to pump the diluent/reagent, and a reagent output port 475. The reagent output port 475 is constructed with a suitable shape and/or elastomeric materials to insure a liquid-tight connection to reagent input port 460 on the test cartridge 402, when the test cartridge is docked to the reagent supply module 470. Reagent supply module 470 has an opening 477 suitably sized to allow monitoring camera 255 (FIG. 3) to image the rotary valve 415. Additionally a window 478 in the reagent supply module 470 is constructed to align with the photometric chamber 409 in the test cartridge. Window 478 allows the photometric light source 293 and photometric detector 295 (FIG. 3) to make optical absorbance measurements on the fluid within photometric chamber 409.

In one embodiment, the size of the vessel within reagent supply module 470 is of sufficient capacity to provide diluent/reagents to dilute and/or stain from ten to about one-hundred samples with a diluent/reagent to sample ratio of 10:1 to about 250:1. The reagent supply module 470 further can include a self-priming mechanism for priming the liquid reagent and eliminating air bubbles. In such an embodiment, the reagent supply module 470 may include a chamber for collecting waste reagent from the priming process. Once the test cartridge 402 is docked with the reagent supply module 470 the combined pieces perform the same functions as test cartridge 401 except that the reagent supply module 470 replaces the blister pack 417. Inside cell analyzer 200 the vacuum/pressure pump 240 makes connections through manifold 245 to sample driver port 411 and mixture driver port 429. The interfaces between the manifold 245 and these ports are constructed with a suitable shape and/or elastomeric material to ensure an airtight connection so that system controller 250 can control movement of the fluids in the test cartridge (see FIG. 3). In such an embodiment the presser foot 230 is not needed.

Figure 7A:
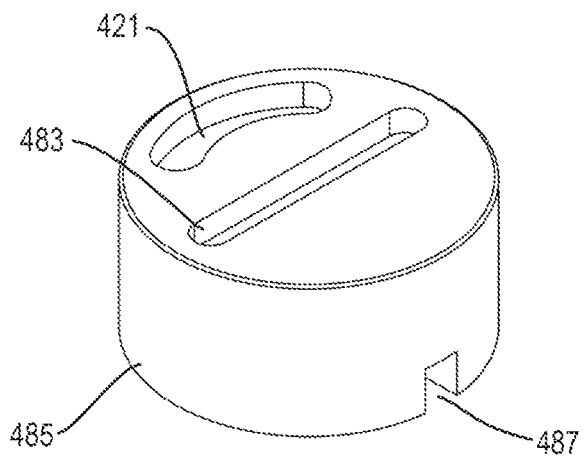
FIG. 7A is a perspective bottom view of a metering chamber formed in the face of a valve stem of a rotary valve.
Figure 7B:
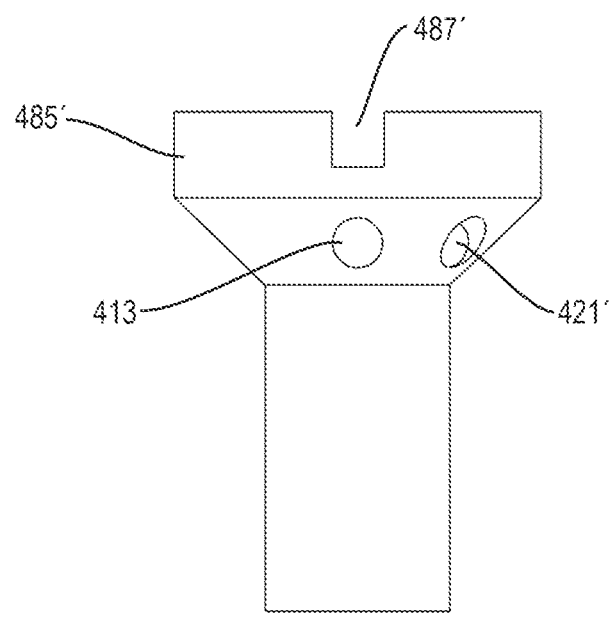
FIG. 7B is a side view of a valve stem of a rotary valve with a pass-through conduit, which serves as a metering chamber, with a metering chamber.

The only volume that is measured precisely is the metered volume of the original biological sample. Various means for metering a small volume of liquid are well known in the art. Two devices that are well suited for low cost, single use applications according to the present invention are shown in FIG. 7A and FIG. 7B. FIG. 7A shows the face of a cylindrical valve stem 485 of a rotary face valve. Metering chamber 483 is formed in the face by highly precise manufacturing processes such as injection molding. The chamber 483 is narrow and tubular in shape and centered in the face of the cylindrical stem 485. A slot 487 in the top of stem 485 acts as a valve indexer to indicate the position of the valve stem 485. Also formed in the face of valve stem 485 is an auxiliary connector 421, which has a circular shape. When assembled into the rotary valve 415 (FIGS. 4 and 5), metering chamber 483 is able to connect between ports in the valve which are 180 degrees apart, while auxiliary connector 421 connects between other ports which are 60 degrees apart. As will be explained with reference to FIG. 8A-8F, system controller 250 is able to control movement of the fluids by rotating valve stem 485 and by positioning the valve according to the valve indexer 487 according to preprogrammed sequences. Thus in a first position, the metering chamber 483 can be connected to the input port 407 (FIG. 4 and FIG. 5) and filled with the biological sample, and then by rotating valve stem 485, the volume contained within metering chamber 483 can be isolated and transferred for analysis.

FIG. 7B is a side view of a valve stem 485' with a metering chamber formed as a pass-through conduit 413 in the tapered seat of valve stem 485'. Pass-through conduit 413 is able to connect with fluidic channels in rotary valve 415 which are 180 degrees apart. Also shown in FIG. 7B is auxiliary fluidic connector 421', which provides connections to adjacent fluidic channels which are 60 degrees apart.

When assembled in the rotary valve 415 (FIG. 4 and FIG. 5) having a tapered seat to receive valve stem 485', pass-through conduit 413 can be connected to input port 407 (FIG. 4 and FIG. 5), filled with the biological sample, and then by rotating valve stem 485', the volume of sample contained within pass-through conduit 413 can be isolated and transferred for analysis. FIG. 7B also shows auxiliary fluidic connector 421', which provides fluidic connections to adjacent fluidic channels on the test cartridge according to the position of the valve indexer 487'. It will be appreciated that the rotary face valve of FIG. 7A and the tapered seat valve of FIG. 7B are alternate embodiments for isolating sample and controlling fluidic paths. Therefore, in the descriptions that follow references to metering chamber 483 in a rotary face valve will be equally applicable to pass-through conduit 413 in a tapered seat valve.

Figure 8A:
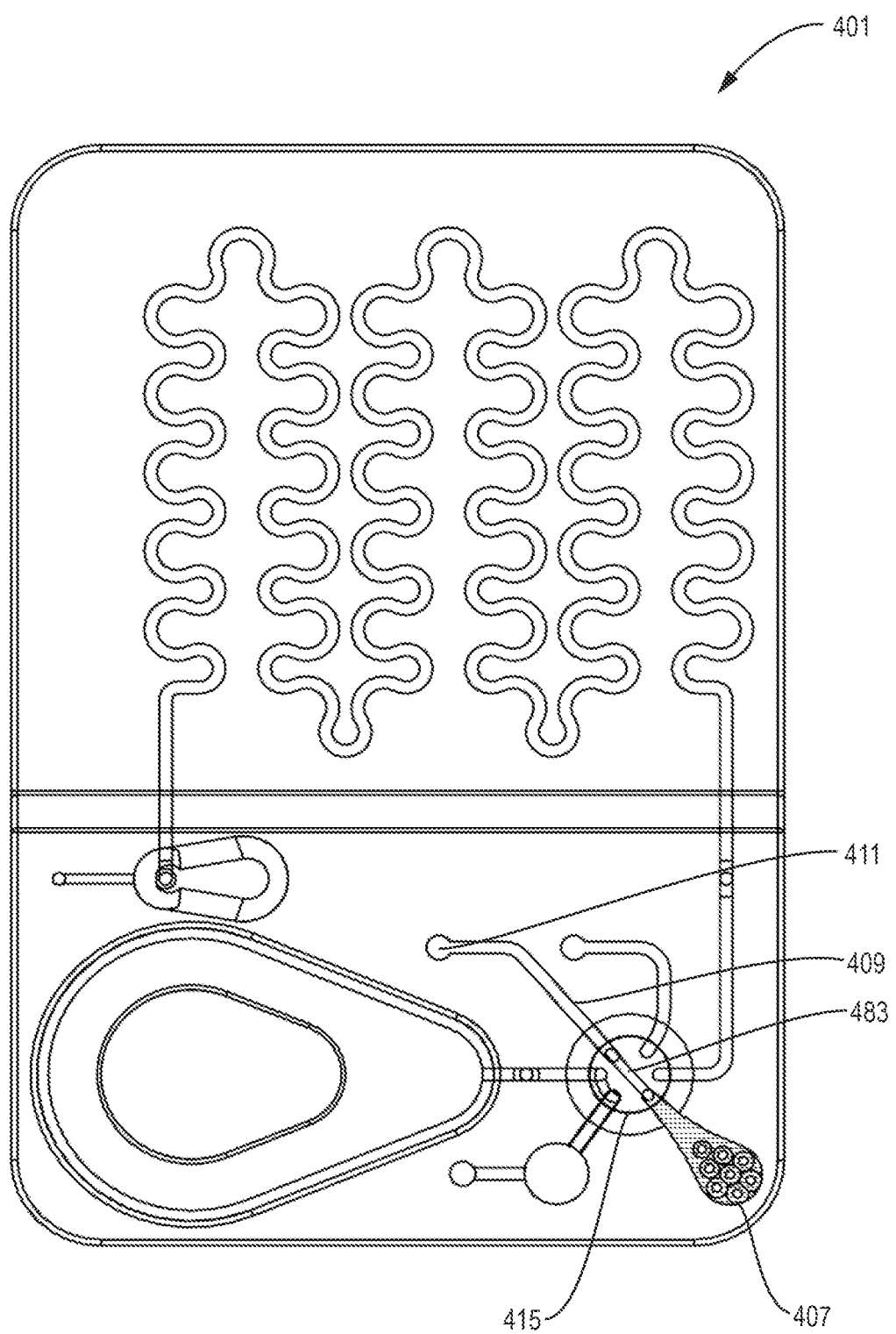
FIG. 8A is a plan view of an illustrative test cartridge showing a sample of whole blood deposited in the input port area.

Now turning our attention to FIGS. 8A through 8F, and with reference to FIG. 3, a sequence of operations will be illustrated that enable cell analyzer 200 to perform automated microscopic cell analysis on a biological sample without skilled operator interactions. In FIG. 8A a sample is shown deposited into input port 407, which is in fluid communication with rotary valve 415. As illustrated in FIG. 8A, the stem 485 (FIG. 7A) of rotary valve 415 is in a first position wherein the metering chamber 483 (FIG. 7A) is aligned with the sample input port 407 and the sample driver port 411. A vacuum, supplied by the analyzer to sample driver port 411, draws the sample from the input port 407 into the metering chamber 483 and into the photometric chamber 409. When the photometric chamber 409 has been filled with sample, the system controller 250 (FIG. 3) collects absorbance data from the undiluted sample using the photometric light source 293 (FIG. 3) and photometric detector 295 (FIG. 3). As will be understood by those skilled in the art, suitable choice of optical wavelengths and chamber geometry and analysis of the light passing through the biological sample can be used to determine concentrations of certain analytes in the sample such as hemoglobin.

Figure 8B:
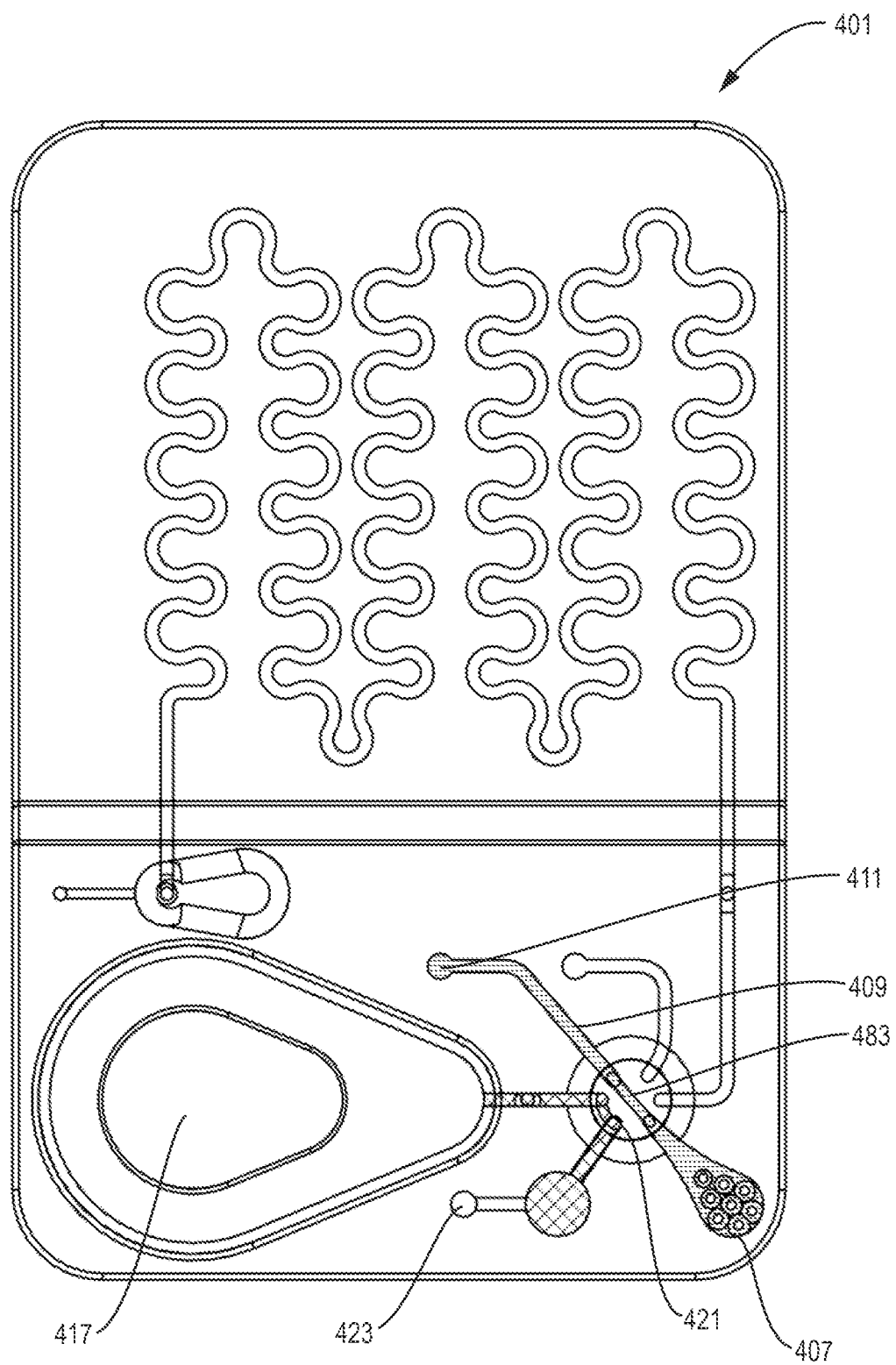
FIG. 8B is a plan view of the test cartridge of FIG. 8A showing initial movement of the sample and reagent with the rotary valve in the first open position.

By illustration and with reference to FIG. 8B, cartridge 401 is shown with a diluent/reagent contained in a blister pack 417. When rotary valve 415 positioned such that the metering chamber 483 is aligned with the input port 407 and photometric chamber 409, auxiliary connector 421 provides a fluid communication path between the blister pack 417 and vent 423. When pressure is applied to the blister pack 417 by presser foot 230 (FIG. 3), diluent/reagent is released and flushed through auxiliary connecter 421 thereby priming the channels and removing air bubbles through vent 423.

Figure 8C:
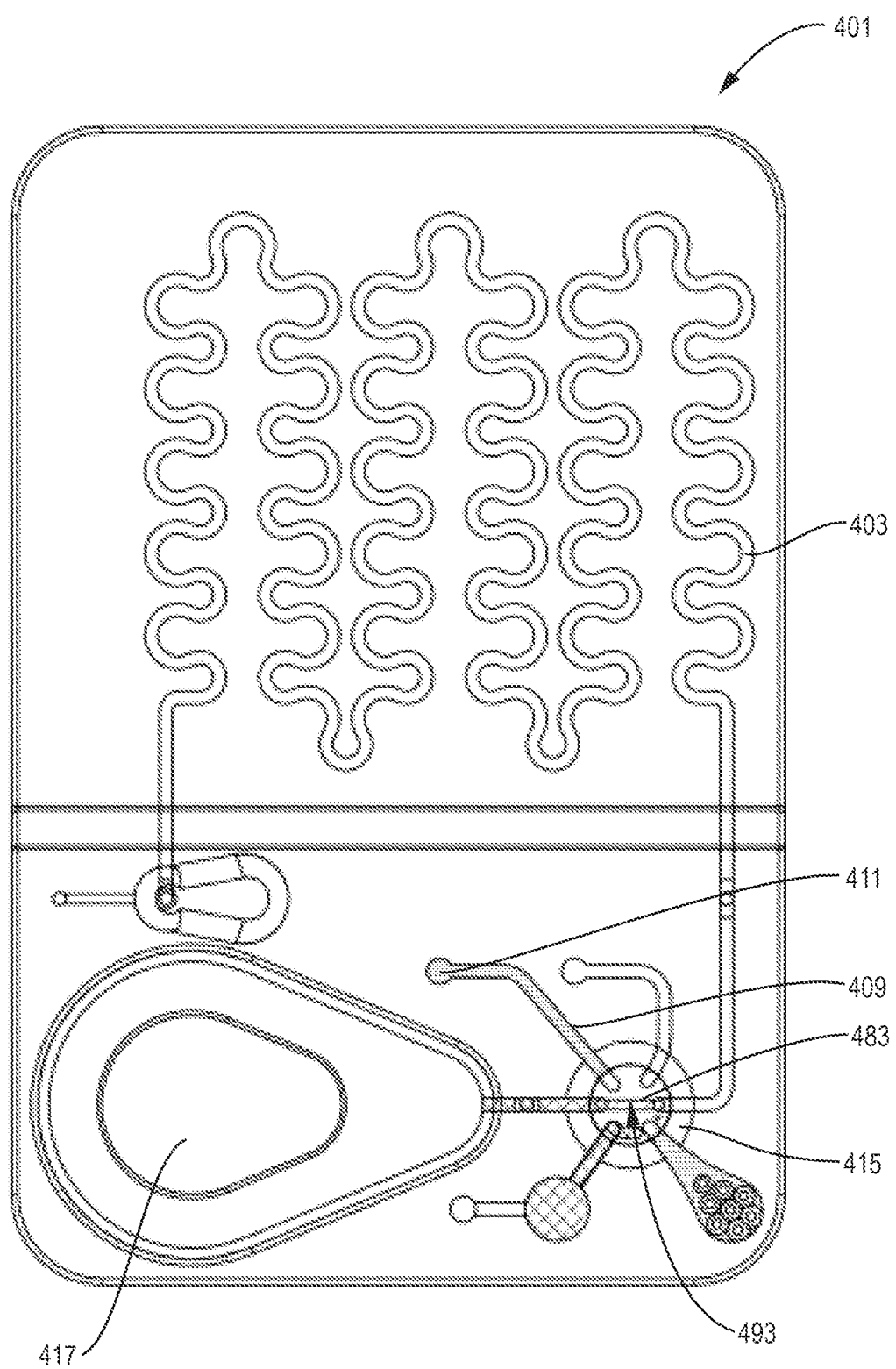
FIG. 8C is a plan view of the test cartridge of FIG. 8B with the valve in the second open position.

FIG. 8C shows rotary valve 415 turned counterclockwise 60 degrees to a second position, which isolates a predetermined amount of sample in the metering chamber 483. In this second position the stem 485 of rotary valve 415 is positioned such that the metering chamber 483 is in fluid communication with blister pack 417 and the serpentine imaging chamber 403.

Figure 8D:
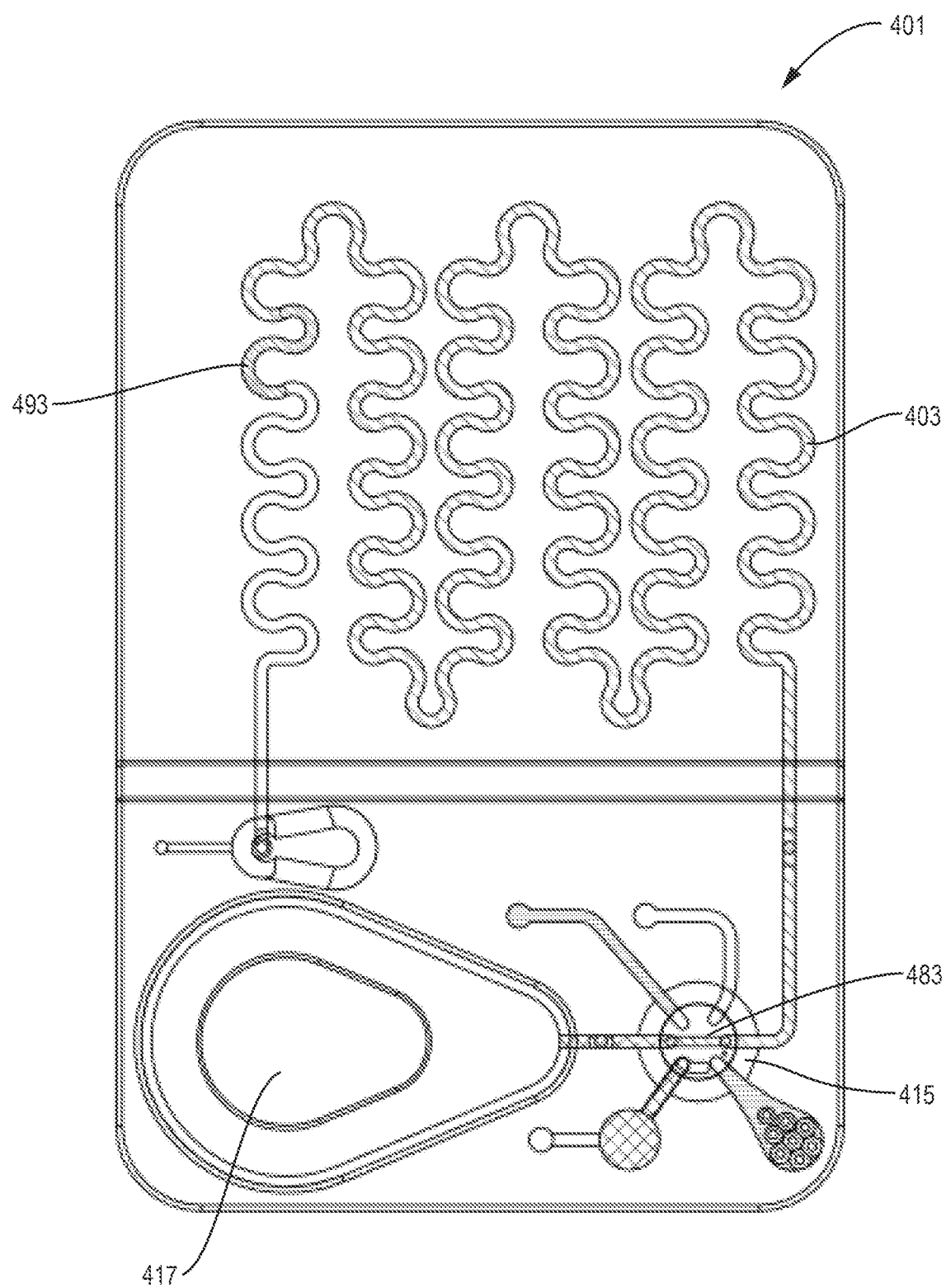
FIG. 8D is a plan view of the test cartridge of FIG. 8C illustrating the sample and the reagent in the imaging chamber.

In FIG. 8D, the rotary valve 415 is shown in the same position as in FIG. 8C but following operation of the presser foot 230 which applies pressure to the blister pack 417. As illustrated by the shaded area, the diluent/reagent from blister pack 417 and the isolated sample 493 from the metering chamber 483 are transferred into the imaging chamber 403. A minimum volume of reagent of three times the volume of the pass-through conduit 413 is needed to flush the entire sample from the rotary valve 415. According to the analysis being conducted, a sufficient volume of the reagent is pushed through the rotary valve 415 to completely wash out the isolated sample and to achieve the approximate dilution ratio desired.

Figure 8E:
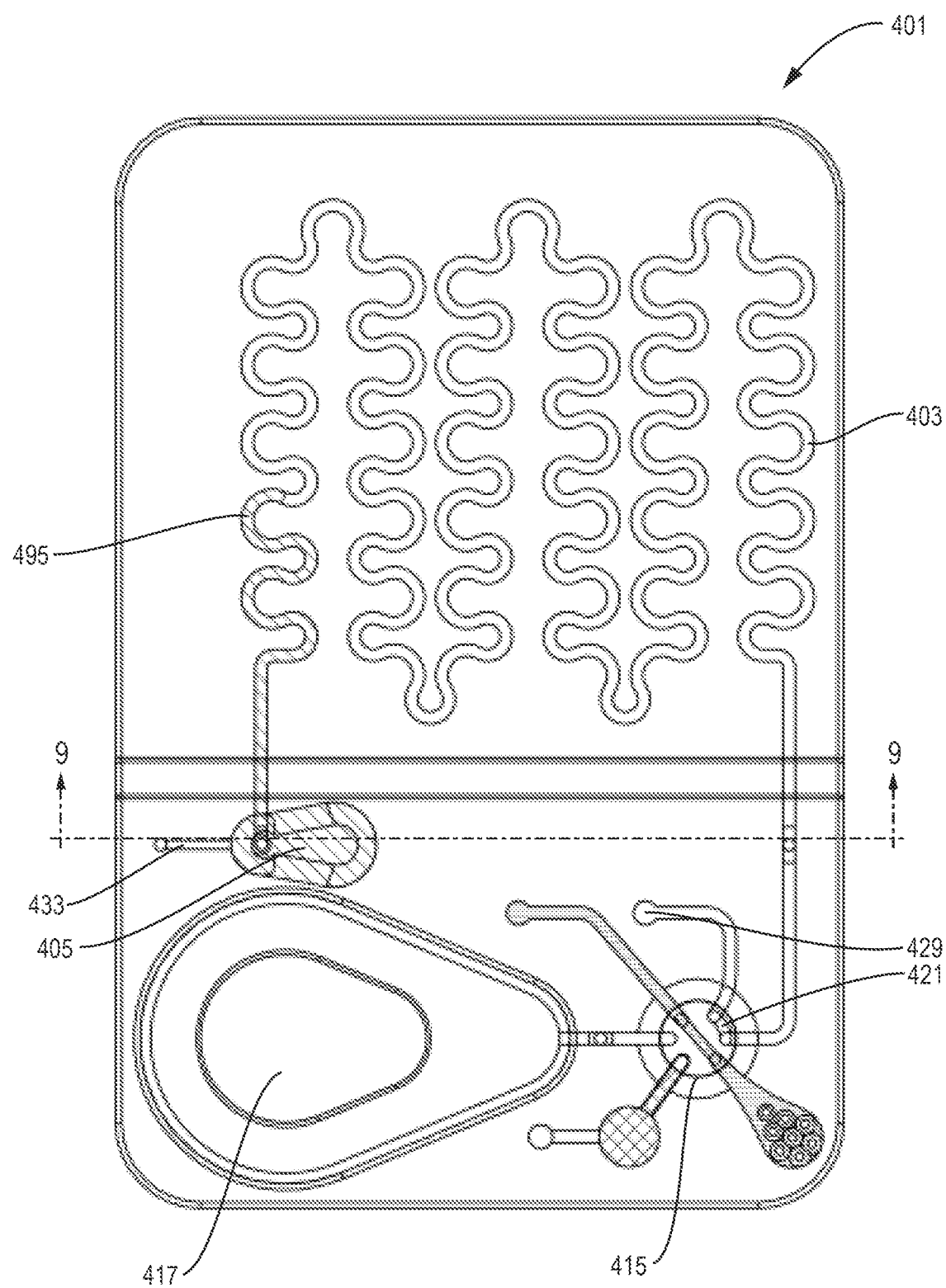
FIG. 8E is a plan view of the test cartridge of FIG. 8D illustrating the sample and most of the reagent positioned in the mixing chamber.
Figure 8F:
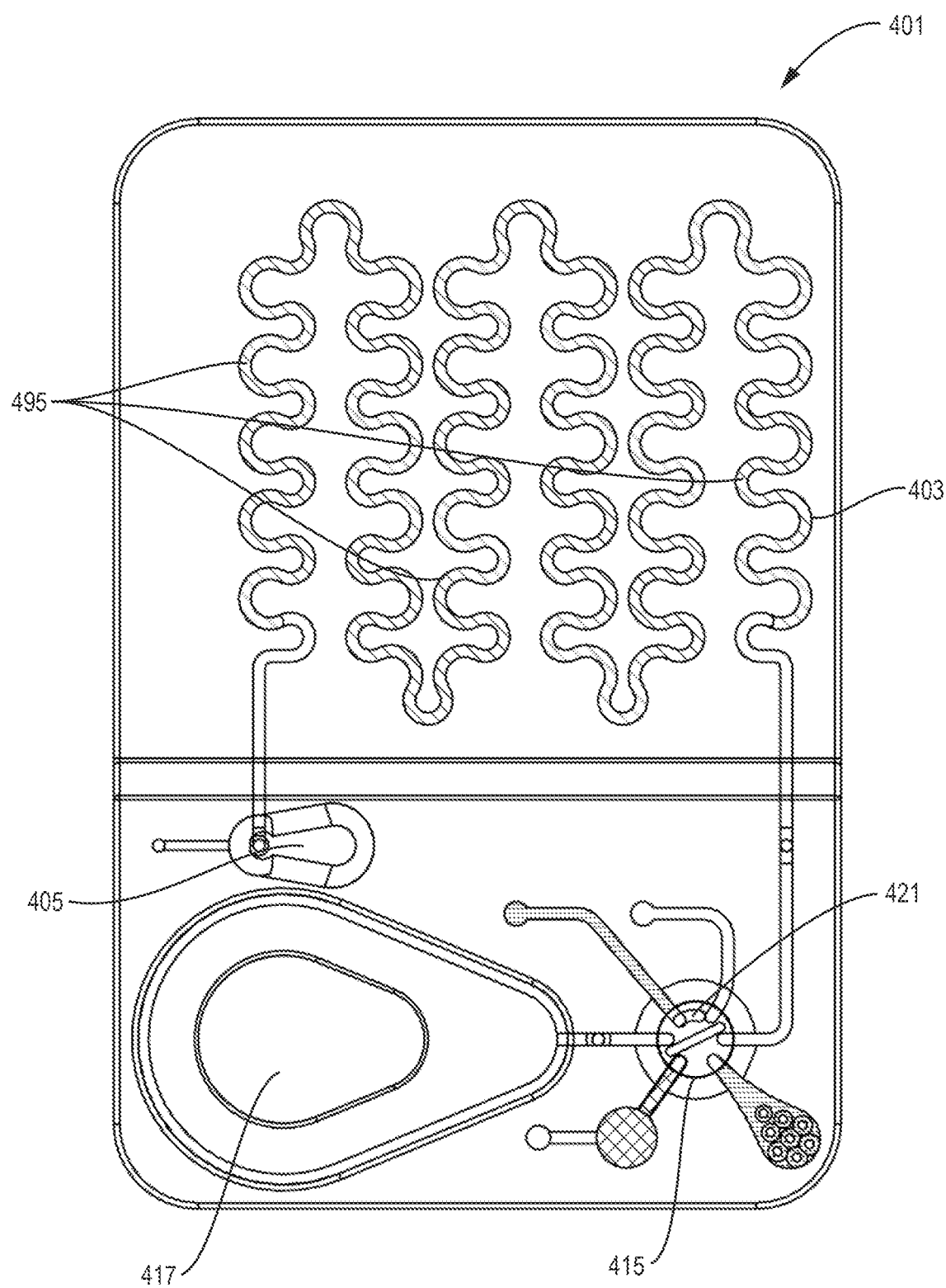
FIG. 8F is a plan view of the test cartridge of FIG. 8E illustrating all of the sample and the reagent positioned in the imaging chamber and the valve in a final, closed position.

In FIG. 8E the rotary valve 415 is shown turned counterclockwise 120 degrees from its previous position shown in FIG. 8D to its third position, wherein auxiliary connector 421 is aligned with mixture driver port 429 and imaging chamber 403. Vacuum/pressure pump 240 of cell analyzer 200 (FIG. 3) supplies pressure to mixture driver port 429 and pushes all of the mixture of sample and diluent/reagent from the imaging chamber 403 into passive mixing chamber 405. As the mixture enters passive mixing chamber 405, air within the chamber is vented through vent port 433. Once all of the mixture of sample and diluent/reagent has been transferred to the passive mixing chamber 405, vacuum/pressure pump 240 applies a controlled vacuum to mixture driver port 429 such that the mixture is pulled back into the imaging chamber 403. A preprogrammed sequence of pushing the mixture into the passive mixing chamber 405 and pulling it back into the imaging chamber 403 is repeated to achieve a final mixture 495 that is free from cell clumping and overlapping after the cells settle to the bottom of the imaging chamber 403. In the final movement of the mixture 495, it is positioned entirely within the imaging chamber 403 as illustrated in FIG. 8F. We have found that that in most instances, pushing the sample and diluent/reagent into mixing chamber 405 and pulling it out is sufficient to provide a uniform mixture. Further, the mixture remains substantially uniform when it is transferred into serpentine imaging chamber 403. It should also be noted that the mixing chamber 405 could be located at the beginning of the imaging chamber 403.

FIG. 8F illustrates the final step of the sample preparation sequence. At this point in the preprogrammed sequence, the entire final mixture 495 has been withdrawn from the passive mixing chamber 405 and is positioned in the imaging chamber 403. When this position is achieved, the rotary valve 415 is rotated counterclockwise approximately 30 degrees to the position shown in FIG. 8F, whereby it is not in fluid communication with any fluidic channel in rotary valve 415, thereby blocking further fluid communication with the imaging chamber 403 so that no further movement of the final mixture 495 can take place.

Figure 9:
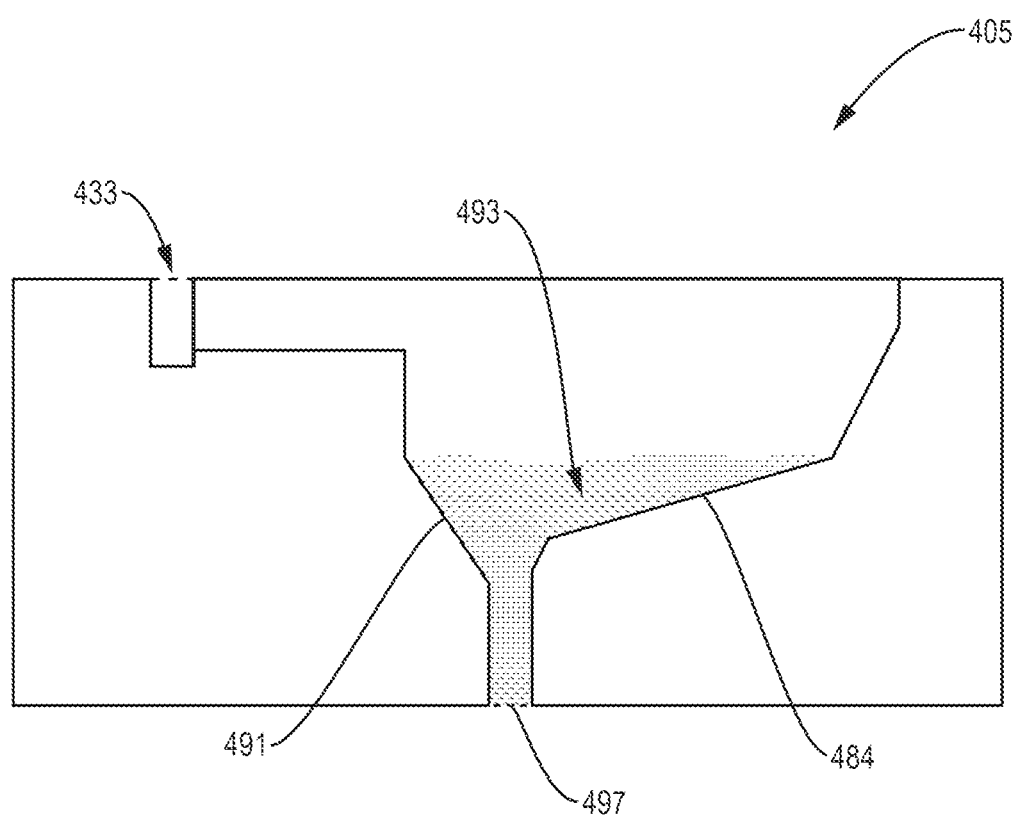
FIG. 9 is an side elevation view of a cross section of the passive mixing chamber taken through line 9-9' of FIG. 8E.

FIG. 9 shows a cross section of the passive mixing chamber 405. The chamber is referred to as "passive" because as illustrated, it does not contain any active mixing element such as a bead or spin-bar. Such devices may be used in some embodiments, but we have found that an adequately sized chamber as depicted in FIG. 9 is simpler and provides excellent mixing of the sample and reagent. In operation the diluent/reagent and sample 493 are driven by vacuum/pressure pump 240 (FIG. 3) and enter and exit the chamber through mixing chamber opening 497. As liquid enters the chamber, air within the chamber escapes through vent port 433. The cross section of passive mixing chamber 405 illustrates wall geometry that increases smoothly in size from the bottom to the top such that the mixture entering from below expands into a larger volume. The chamber 405 may have asymmetrical sloped walls 484 and 491 to promote mixing of the sample and reagent and for removing bubbles from the mixture. After all of the mixture is in the chamber, air bubbles may be introduced to the chamber by vacuum/pressure pump 240 through mixing chamber opening 497. These air bubbles further promote mixing and subsequently escape through vent port 433. The choice of materials used to fabricate the passive mixing chamber 405 should take into consideration the wetting properties of the specific 1 diluent/reagent(s) being utilized in the test cartridge 401. The properties of the material, among other requirements, should ensure that liquid surface tension will pull back all of the liquid in contact with the side walls of the chamber when the vacuum/pressure pump 240 empties the chamber through mixing chamber opening 497.

Figure 10:
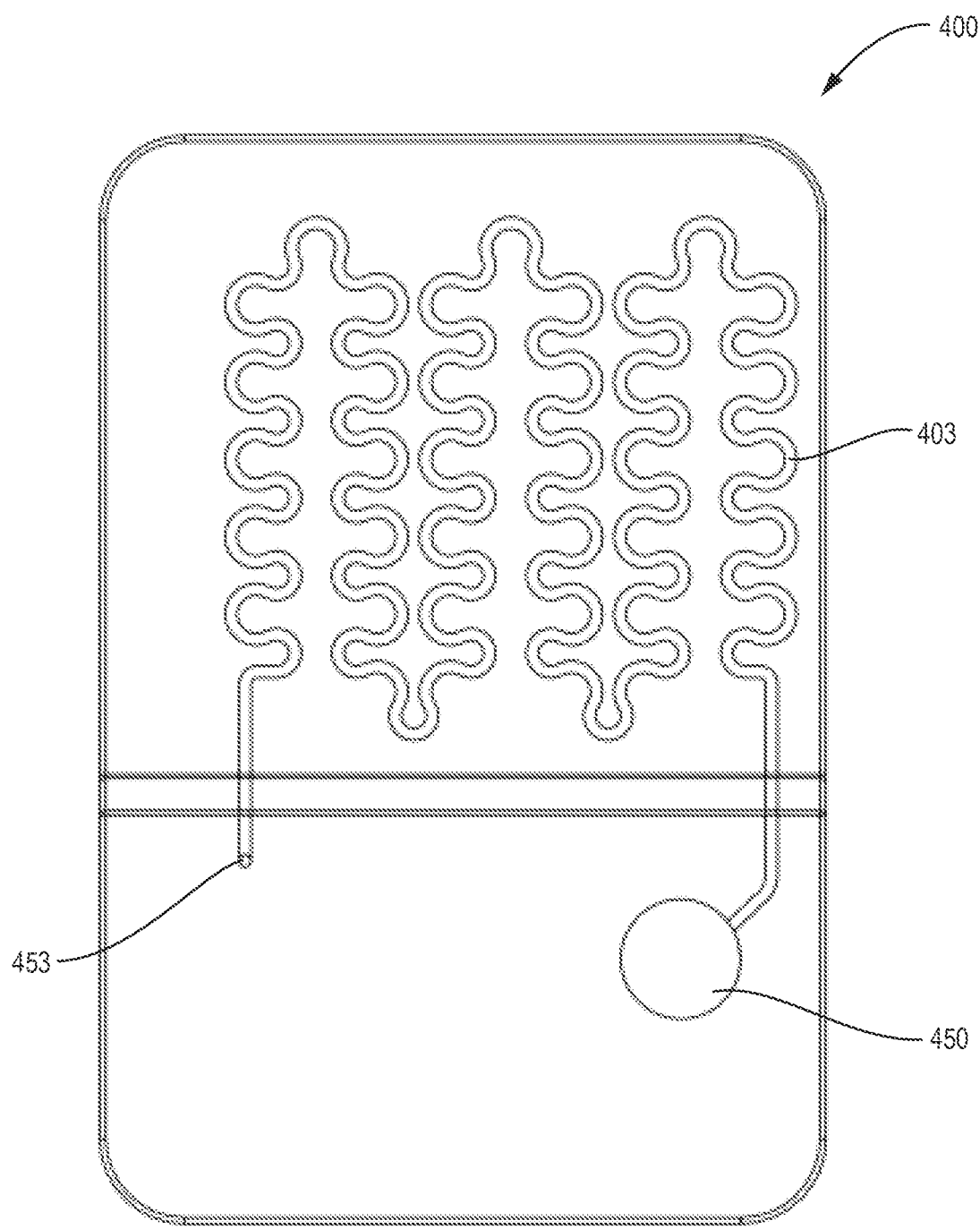
FIG. 10 is a plan view of an alternative test cartridge with sample input port and imaging chamber.

FIG. 10 illustrates test cartridge 900 which comprises an imaging chamber 903 having at one end a sample input port 950, and at the opposite end a vent 953. A user of test cartridge 900 collects a small known volume of whole blood and mixes it manually with a diluent/reagent in a separate single-use sample preparation device (not shown). Once mixed, the entire mixed volume is injected into sample input port 950 at a controlled rate, such that the cells uniformly fill the imaging chamber. Air escapes through vent 953, allowing the sample and diluent/reagent mixture to fill the imaging chamber 903. The form of the imaging chamber is essentially the same as the imaging chamber as described above and shown in FIGS. 8A-8F, except that the volume of the imaging chamber must be sufficient to include all of the mixture of sample and diluent/reagent. Test cartridge 900 can be placed into analyzer 200 (FIG. 3) to count every cell in the mixture of sample and diluent/reagent and for analysis beginning at step 560 of FIG. 11 as described below.

Figure 11:
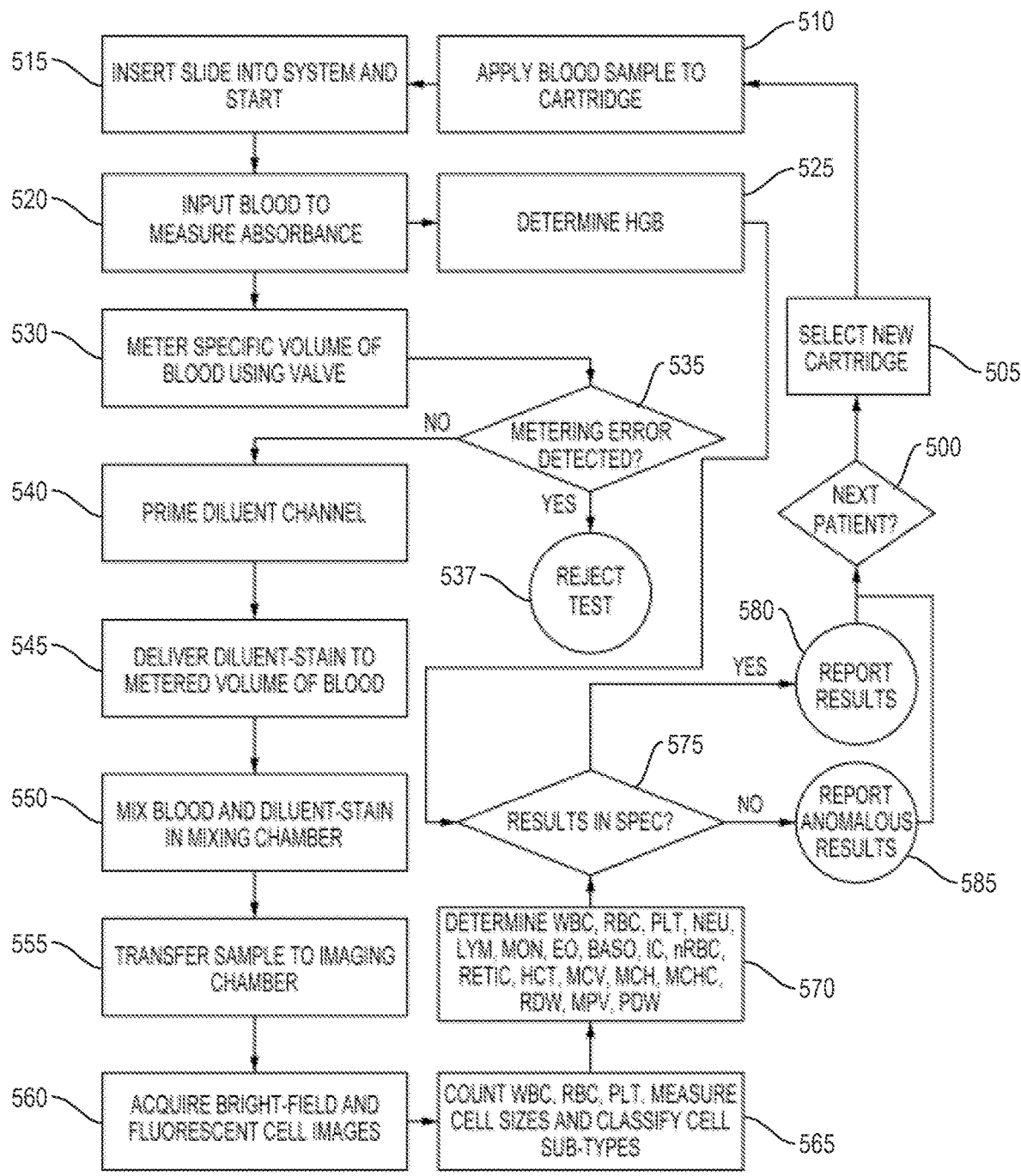
FIG. 11 is a flowchart illustrating the operation of the cell analyzer.

Turning our attention to FIG. 11 we will now describe the overall operation of cell analyzer 200 configured to provide a "CBC with Differential" analysis with reference to the test cartridge 401 illustrated in FIGS. 8A-8F and cell analyzer 200 illustrated in FIG. 3. To obtain the blood sample from a patient presented at box 500, the user first obtains a new test cartridge 401 at box 505 and opens it to expose the input port 407. Blood from a finger prick is applied as illustrated in FIG. 1 at box 510 and the input port 407 is covered. The user inserts the test cartridge into the cell analyzer 200 at box 515. The test cartridge is moved into the analyzer where mechanical and fluid connections are made between the analyzer and the cartridge as described above with reference to FIG. 3. As a first step of analysis, the sample is drawn into the metering chamber passing through and into photometric chamber 409 (FIG. 8A). Absorbance of the blood is measured at box 520. Data from absorbance measurements are used to determine hemoglobin concentration. At box 530 sample in the metering chamber 483 is imaged using monitoring camera 255 and analyzed to confirm that the metering chamber was properly filled at box 535. If an error is detected the analysis is terminated at box 537 and the user is alerted to the error and instructed to remove the cartridge and reject the test.

If the pass-through conduit 413 is correctly filled the diluent/reagent channel is primed at box 540 as described above with reference to FIG. 8B. Rotary valve 415 is then turned to the position shown in FIG. 8C to isolate the sample and to allow diluent/reagent to wash the metered volume of blood out of the pass-through conduit 413 at box 545 while being imaged by monitoring camera 255. The transfer continues until the monitoring camera 255 confirms that diluent/reagent plus sample has almost filled the imaging chamber as illustrated in FIG. 8D.

Once a sufficient volume of diluent/reagent is transferred, rotary valve 415 is positioned as shown in FIG. 8E and the total volume of sample and diluent/reagent is mixed at box 550. At box 555 the entire volume 495 is transferred to the imaging chamber and rotary valve 415 is positioned as shown in FIG. 8F. Note that by transferring the entire volume of mixed sample 495, all of the metered volume of blood from the original sample plus the unmetered volume of diluent/reagent is positioned in the imaging chamber at box 555.

If test cartridge 400 is used, it is inserted into cell analyzer 200 and analysis begins at step 560. Analysis of test cartridge 401 or 402 continues at step 560 when the x-y stage 225 moves the test cartridge 401 to obtain bright-field and fluorescent images of the entire imaging chamber 403 at box 560. In an alternate embodiment, objective lens 265 and/or digital camera 280 are moved and test cartridge 401 remains stationary. In yet another embodiment objective lens 265 has sufficient field of view to capture the entire imaging chamber 403 without movement. Two digital images of each physical frame of the imaging chamber are transferred to image processor/computer 290 at box 565. One image, taken with bright-field optics, can be compared to the other image taken with fluorescent optics to identify red blood cells, white blood cells and platelets. Further analysis of the white cell sizes and internal structure can identify sub-types of white cells using pattern recognition.

At box 570 comparison of the bright-field and fluorescent images can differentiate mature red cells from reticulocytes and nucleated red blood cells. By dividing each cell count by the known volume of the metering chamber 483, the concentration (cells per unit volume) can be determined. By using a sphering agent the planar sizes of red cells can be transformed into mean corpuscular volume (MCV). Combining the red blood cell count with MCV and the volume of the metering chamber 483 allows the calculation of hematocrit (HCT) and red cell distribution width (RDW). Further calculations using the separately measured HGB from box 525, combined with the RBC count gives mean corpuscular hemoglobin (MCH), and mean corpuscular hemoglobin content (MCHC).

At box 575 the measured results are compared with previously defined limits and ranges for the particular patient population and determination is made whether the results are within or outside normal expected ranges. According to this determination results within normal ranges are reported in box 580 and results that are outside the normal ranges are reported in box 585.

As noted above, another embodiment of the invention is to perform a CBC on a known or measured volume of diluted sample. In this embodiment, every cell and platelet in the known volume of diluted sample is counted. If the volume of the diluted sample and the dilution ratio is known, the number of cells and platelets per unit volume of sample can be determined. A hematology analyzer can be provided to perform the CBC on a known volume of diluted sample, utilizing a single use disposable test cartridge. The length and depth of the imaging chamber will depend upon the dilution ratio and the volume of the known diluted sample. For instance, a 20 uL sample of whole blood may be diluted 50 to 1 producing 1000 uL of diluted sample. 20 uL of the diluted sample may then be taken to be analyzed. Every cell and platelet in the diluted sample is counted, either directly or by statistical representation. The 20 uL of known diluted volume corresponds to 0.4 uL of whole blood. The volume of the imaging chamber must be at least 20 uL in order to contain all of the known volume of diluted sample.

The dilution ratio must be sufficient to prevent crowding or overlapping when the cells settle to the bottom of the imaging chamber. The dilution ratio also depends on the depth of the imaging chamber as explained above. The volume of diluted blood must be sufficient to contain enough white cells to be significantly representative of the whole blood sample. For example, the average number of white cells in whole blood of a healthy patient would be approximately 5000 per microliter. In 0.4 uL of whole blood, there would be about 2000 white cells. However, in a sick patient, or one being treated with chemotherapy, the white cell count could be as low as 500 white cells per microliter. In this case, the number of white cells in a 0.4 uL diluted sample would be about 200 cells, which may be an inadequate number of white cells to be clinically significant. In this case, a larger volume of diluted sample may be desirable. However, the time to image and count every cell in the known volume of diluted sample increases as the volume of the diluted sample increases.

Figure 12:
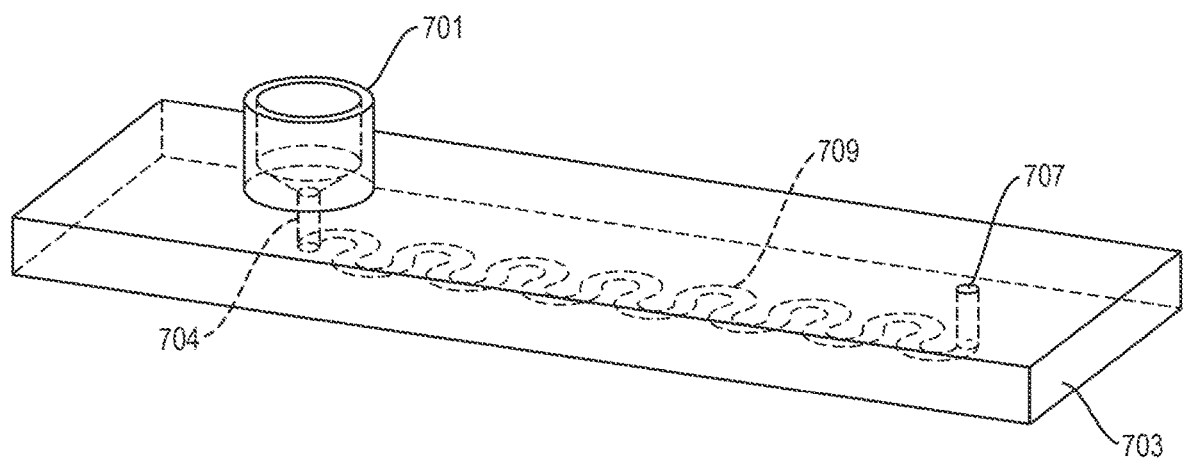
FIG. 12 is a plan view of a test cartridge with sample cup and serpentine imaging chamber.

The hematology analyzer utilized to perform a CBC on a known diluted volume of sample will comprise an automated microscope for imaging the cells in the imaging chamber of a test cartridge, similar to the one described above and shown in FIG. 3, except that it need not have a presser foot and valve driver. In one embodiment, the dilution step may be performed manually with pipettes and a mixing tube or beaker, and outside of the analyzer, in which case the dilution ratio will be known. A known volume of the mixture may be deposited in a sample cup 701 FIG. 12 on a test cartridge 703 having a serpentine imaging chamber 709. The sample cup may be in fluid communication to the imaging chamber 709 by a channel 704 at one end of the imaging chamber 709. At the opposite end of the serpentine chamber 709 is a vent hole 707. When the test cartridge is inserted into the analyzer, the vent hole 707 interfaces with the vacuum/pressure source of the analyzer. The diluted sample is drawn into and positioned within the imaging chamber 709, when a vacuum is applied at the vent hole 707, such that its entire volume will be located within the imaging chamber. The diluted sample may also be pushed back into the sample cup by pressure applied at the vent hole and then pulled back into and positioned in the imaging chamber for the purposes of mixing the diluted sample, similar to the way described above with reference to the mixing chamber 405 in FIG. 8e. The sample cup may be of the same shape and format as the mixing chamber 405 in FIG. 8e to facilitate mixing if this is required. For instance, if the known volume of diluted sample is deposited in the sample cup and the test cartridge is not inserted in the analyzer for cell analysis immediately, the cells in the diluted sample may settle to the bottom of the sample cup. In this case, mixing may be necessary. Once the diluted sampled is positioned in the imaging chamber, the analyzer may perform a CBC on the diluted sample as described above.

Figure 13:
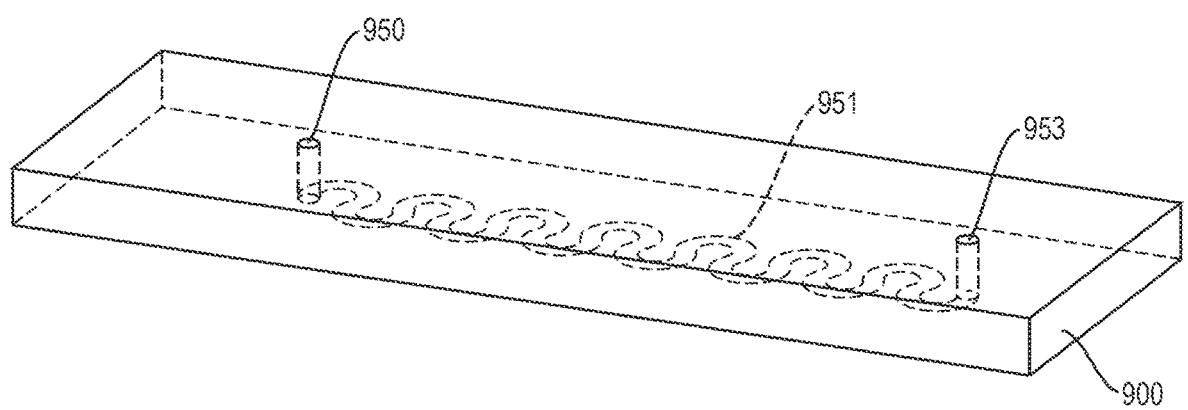
FIG. 13 is a plan view of a test cartridge with a serpentine imaging chamber.

Alternatively, a measured volume of sample and a measured volume of diluent/reagent may be mixed manually, and a portion of the mixture having a known volume may be inserted, at a controlled flow rate to prevent crowding and insure a uniform distribution of cells, into a test cartridge having a serpentine imaging chamber as illustrated in FIG. 13. The dimensions of the serpentine path are chosen in accordance with the dilution ratio, the known volume of the mixture, and the guidelines set forth above. Every cell in the known volume of the mixture may be counted and analyzed as set forth above.

In another embodiment, the dilution and sample preparation step and may be performed by an analyzer utilizing a probe for aspirating a whole blood sample, a shear or face valve for isolating a predetermined volume of sample, a supply of diluent/stain, a syringe pump for metering and dispensing a known amount of diluent/stain in a mixing bowl for mixing the sample and diluent/stain, solenoid rocker valves or pinch valves for controlling the movements of fluids, vacuum and pressure sources, and a disposable single use test cartridge. The shear valve is in fluidic communication with the analyzer probe that aspirates blood samples. A sample is drawn through the probe and into the shear valve, which may be turned, trapping a predetermined amount of sample. The shear valve is further turned to a position where it is in fluidic communication with a pressure source and the mixing bowl. The isolated blood sample is pushed into the mixing bowl by the pressure source. The syringe pump is in fluidic communication with diluent/stain supply and the mixing bowl. The syringe pump dispenses a predetermined amount of diluent/stain into the mixing bowl. The blood sample and diluent/stain can be mixed in the bowl by pushing air through the probe and bubbling the air through the mixture. When mixed, a portion of the mixture may be drawn into a metering chamber of known volume and in fluidic communication with the mixing bowl. Optical edge detecting sensors are used to control the flow of the mixture into the metering chamber. The test cartridge illustrated in FIG. 13 is used as a single use disposable cartridge with the hematology analyzer. It is inserted into the analyzer such that the channel 950 FIG. 13 at one end of the serpentine imaging chamber 951 interfaces with, and is in fluidic communication with, the metering chamber. A vacuum is applied to the opposite end of the serpentine path through vent hole 953, FIG. 13, and the portion of the diluted sample in the metering chamber is drawn into, and positioned in, the imaging chamber, at a controlled rate to prevent crowding and to insure uniform distribution of the cells, for CBC analysis as described above. The dimensions of the serpentine path will depend upon the dilution ratio, the volume of the portion of the mixture and the guidelines noted above. One drawback to this arrangement is that the shear valve, metering chamber, mixing bowl, metering chamber, and connecting fluid channels must be flushed between every sample. Such analyzers also require frequent calibration and maintenance.

Figure 14:
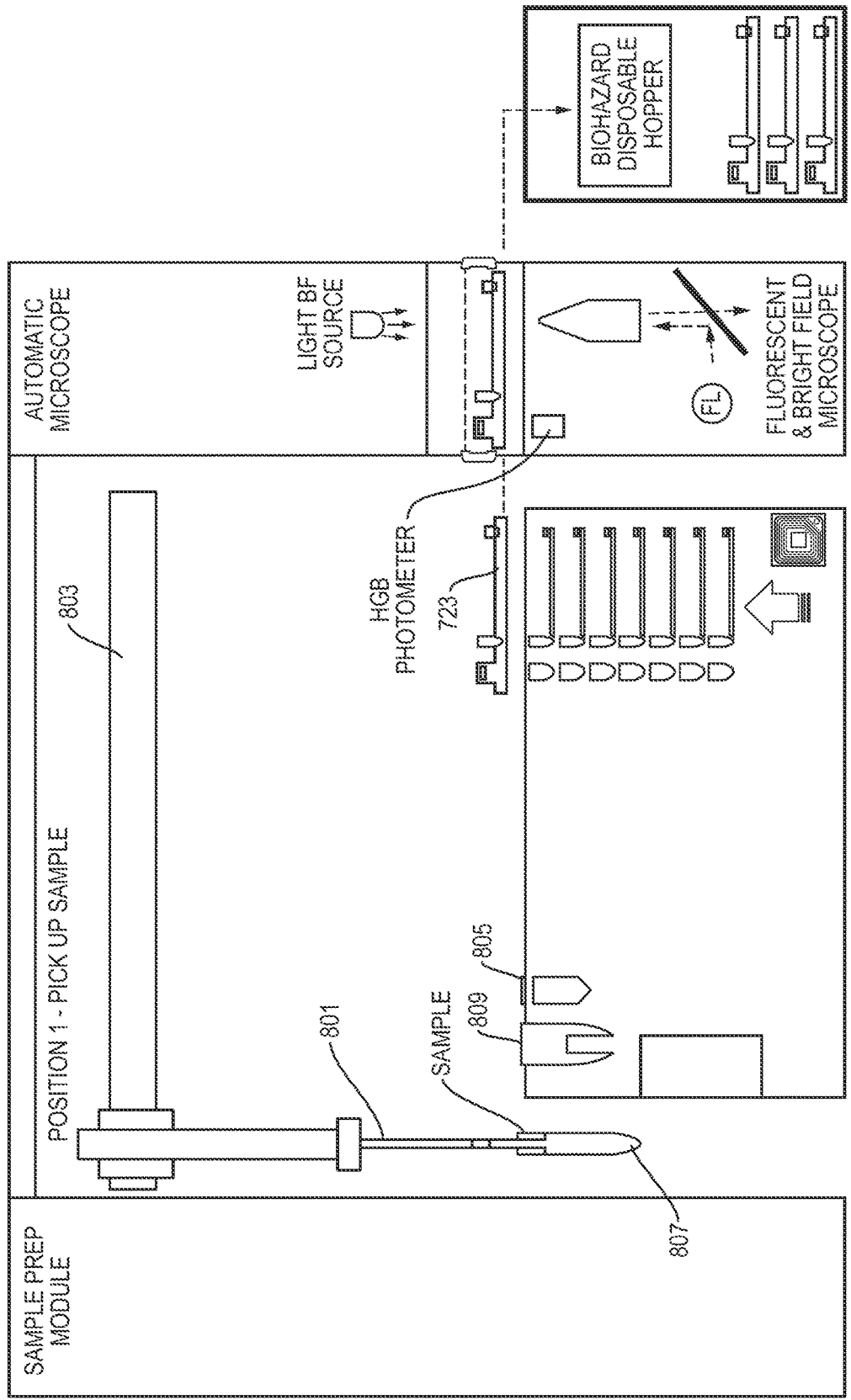
FIG. 14 is a plan view of a hematology analyzer using a single test disposable test cartridge illustrated in FIG. 15.
Figure 15:
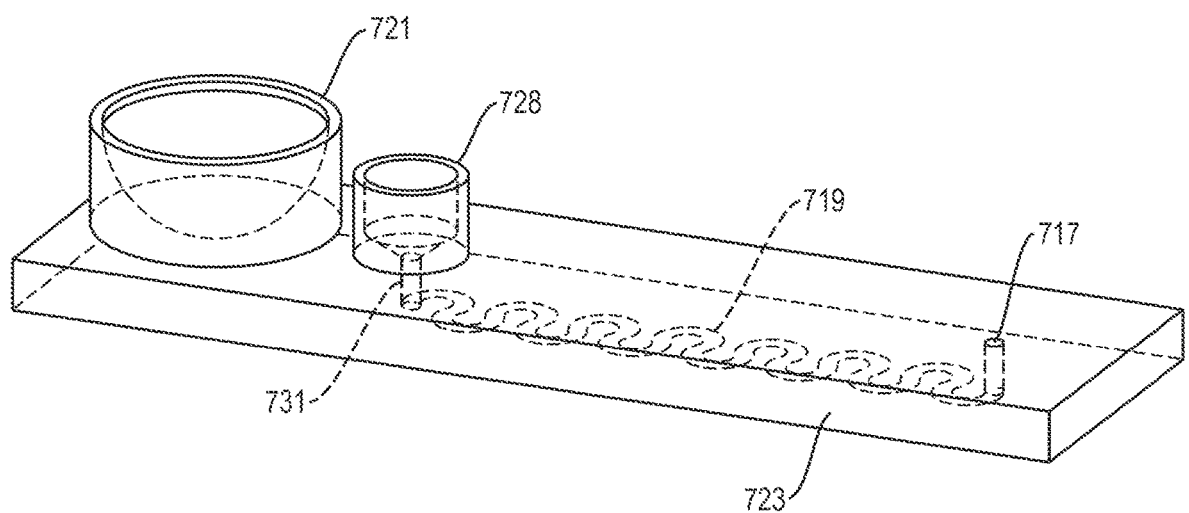
FIG. 15 is a plan view test cartridge showing a mixing bowl, sample cup, and serpentine imaging chamber.
Figure 16A:
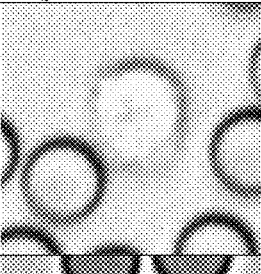
FIGS. 16A and 16B show bright-view and fluorescent images of the same cells that were collected according to the present invention.
Figure 16A:
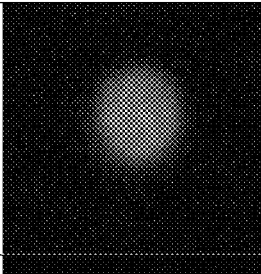
Figure 16A:
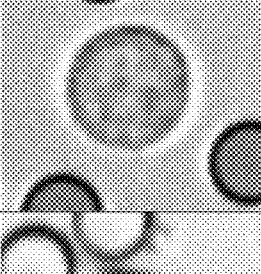
Figure 16A:
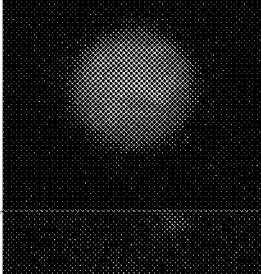
Figure 16A:
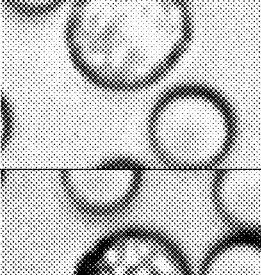
Figure 16A:
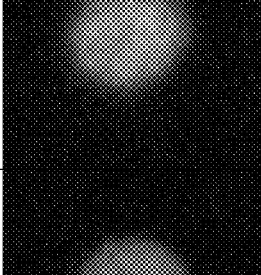
Figure 16A:
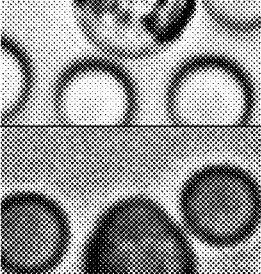
Figure 16A:
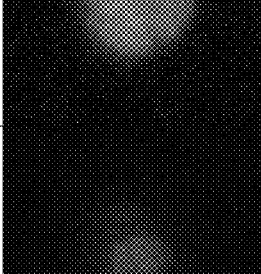
Figure 16A:
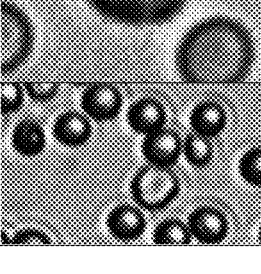
Figure 16A:
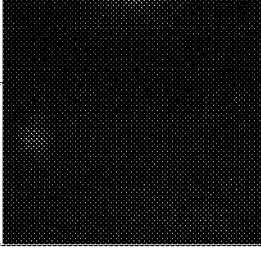
Figure 16A:
Figure 16A:
Figure 16B:
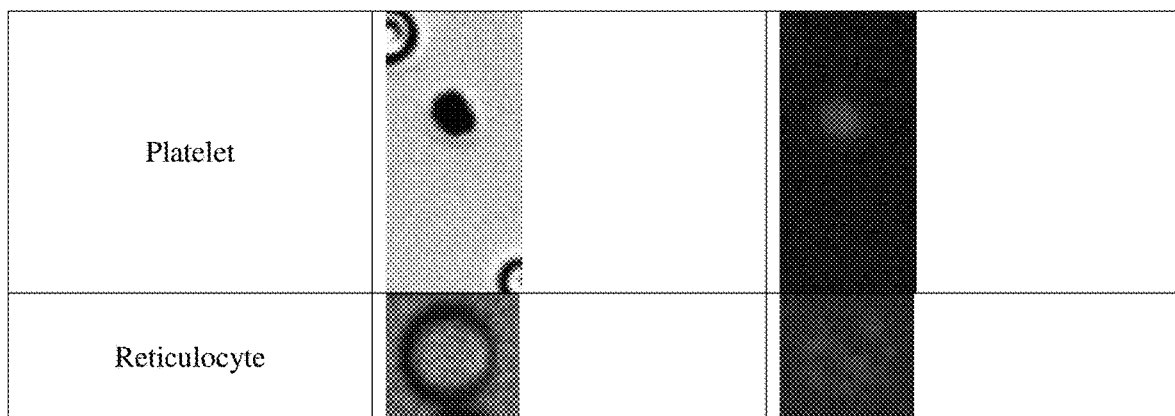

In another embodiment, the dilution step and metering step may be performed with a test cartridge having a mixing bowl and diluted sample cup on the test cartridge. The analyzer includes a sampling probe, diluent/stain reservoir, precise diluter syringe pump, and wash station. In this case, the probe may be attached to a transfer arm mounted on the base of cell analyzer 200 FIG. 3, which can move vertically in the z direction with respect to stage 225 FIG. 3. The transfer arm can move horizontally along a linear axis such that it can be vertically aligned with the wash station or the diluent/reagent reservoir, or sample container. A schematic of the analyzer is illustrated in FIG. 14. The dilution step is as follows. The probe 801 FIG. 14 moves along its linear axis 803 until it is aligned vertically with the diluent/stain reservoir 805. It then moves downward in the vertical direction until the tip of the probe is submerged in the diluent/stain 805. It then aspirates a known amount of diluent/stain, e.g. 1000 uL. The probes moves upward and horizontally along axis 803 until it is aligned with the sample container 807. After aspirating 3 uL of air, it moves downward in the vertical direction until the tip of the probe is well submerged in the sample in sample container 807. The analyzer then aspirates 20 uL of sample, such as whole blood, from the sample container, after which the probe is moved upward and above the sample container, where it aspirates another 3 uL slug of air. The probe then moves along the linear axis 803 until it is aligned vertically with the mixing bowl 721 FIG. 15 on test cartridge 723. The probe is then lowered vertically until the tip of the probe is just above the bottom of the mixing bowl 721. The analyzer then dispenses the blood sample and the diluent/stain into the mixing bowl 721 on the test cartridge 723. This sequence of steps insures that the entire aspirated blood sample is flushed out of the probe by the diluent/stain reagent and into the mixing bowl. The analyzer may mix the blood and diluent mechanically such as by moving back and forth along its axis 803 or by bubbling air through the mixture, or by aspirating the mixture and redispensing it into the mixing bowl, or by other methods. After the sample and diluent/stain are mixed, the analyzer aspirates 20 uL of the mixture. This corresponds to 0.4 uL of undiluted sample. The probe is then moved upwards and moved along the linear axis 803 FIG. 14 until the probe is aligned with the diluted sample reservoir 728 FIG. 15. The probe is lowered and the 20 uL mixture of sample and diluent/stain is dispensed into sample cup 728 FIG. 15, which is in fluidic communication with one end of the serpentine path 719 through channel 731. The mixture may be pulled through the serpentine path of imaging chamber 719 at a controlled rate by a vacuum source on the analyzer, which interfaces with vent hole 717 on the opposite end of the imaging chamber from the sample cup 728. Alternatively, after the sample is dispensed, the probe may be positioned into vent hole 717, which may also contain a sealing o-ring, and the analyzer aspirates air through the probe at a controlled rate, such as 2 uL per second, to prevent crowding and to insure a uniform distribution of cells. The analyzer positions the entire mixture of sample and diluent/stain in the imaging chamber 719. The dimensions of the serpentine path depend upon the dilution ratio, the volume of the mixture, and the considerations noted above. Another variation would be to utilize a test cartridge without the sample cup, in which case the probe, after it has aspirated the 20 uL of diluted sample, may interface directly with the fluidic channel 731 and dispense the mixture at a controlled rate directly into the serpentine path of imaging chamber 719.

The probe may be washed at the wash station 809 FIG. 14 after aspirating or dispensing blood or diluent/stain or the mixture of sample and diluent/stain to eliminate any solution adhering to the side of the probe. Although this process is not described above, those skilled in the art relating to chemistry analyzers or X-Y dispensing fluid mechanisms will understand the practices and procedures for doing so.

One advantage to this embodiment is the elimination of the shear valve and fluidic tubing and flushing them as well as interconnecting fluidic channels from sample to sample. It also reduces and may eliminate the need for pinch and/or solenoid valves.

The analyzer may process samples in parallel by performing the CBC imaging analysis on the known diluted sample in the imaging chamber of one test cartridge, while the analyzer is simultaneously diluting another sample and depositing it in the imaging chamber of a second test cartridge. This can be done to increase analyzer throughput.

EXAMPLES

Example 1: Information from Bright-Field and Fluorescent Optics

FIG. 16 shows images that were collected using test devices according to the present invention. A fluorescent stain Acridine Orange (AO) was used to differentially stain DNA and RNA of cells in a whole blood sample. The visual images of FIG. 16 were obtained using an Olympus 20××0.4 NA objective lens 265 and a Basler 5 MP digital camera 280. Excitation of the bright-field images in the second column was provided by white light bright-field source 260. Excitation of the fluorescent images in the third column was a 455 nm blue fluorescent light source 270.

White blood cells have significant RNA and DNA and therefore can be seen in the fluorescent images having green and orange structures. The size and shape of the green nuclear structure and overall size of the white cells can be used to differentiate them into sub-groups identified by name in the first column. Notably the basophil and eosinophil sub-groups of white cells have characteristic features in the bright-field image due to the presence of large granules in the cytoplasm. Therefore embodiments of the present invention make use of both bright-field and fluorescent image analysis to differentiate sub-groups of white cells.

Platelets also take up the AO stain but the size of a platelet is significantly smaller than any white cell and can therefore be differentiated. Because red cells lose their nucleus as they mature, they do not have nuclear material to take up the AO stain. Consequently the red cells can be identified as the objects that appear in the bright-field and cannot be seen in the fluorescent field. The immature red cells, called reticulocytes and the nucleated red blood cells (nRBC) have attributes of red cells but also show small levels of fluorescence. Embodiments of the present invention make use of these combined attributes to identify and sub-group red blood cells.

Example 2. Statistical Sampling of the Imaging Chamber

Table 1 illustrates a comparison of CBC parameters obtained according to the present invention and from an automated hematology analyzer.

TABLE 1

| Column1 | # pairs | RBCs | WBCs | ROI | RBC/f | RBC/f(%)- | WBC/f | WBC/f(%) | RBC/WBC |
|---|---|---|---|---|---|---|---|---|---|
| 100% | 9916 | 2455492 | 5125 | 3818.7 | 643.02 | 100.0 | 1.342 | 100.0 | 479.12 |
| 50% | 4958 | 1229669 | 2535 | 1913.7 | 642.56 | 99.9 | 1.325 | 98.7 | 485.08 |
| 25% | 2479 | 623048 | 1285 | 968.5 | 643.28 | 100.0 | 1.327 | 98.9 | 484.86 |
| 10% | 992 | 242197 | 519 | 373.5 | 648.48 | 100.8 | 1.390 | 103.5 | 466.66 |
| 5% | 496 | 126186 | 262 | 197.2 | 639.82 | 99.5 | 1.328 | 99.0 | 481.63 |
| 1% | 100 | 23683 | 63 | 35.6 | 664.61 | 103.4 | 1.768 | 131.7 | 375.92 |

Sample: Low WBC count—approximately 2000/uL (normal is 3,000-10,000/uL).
Magnification: 20×
Number of images: approximately 10,000 bright-field and 10,000 fluorescent
Variable: Column 1—Percentage of total cells use in the calculation
Column #pairs—the number of pairs of images (bright-field plus fluorescent)
Column RBCs—total number of Red Blood Cells counted
Column WBCs—total number of White Blood Cells counted
Column ROI—total Region of Interest. This is the 'effective' number of image frames occupied by actual sample. A frame totally filled with sample/cells is "1". A partial frame (due to an edge or the curved ends of the serpentine shape), is a fraction of a frame (e.g. 0.567).
Column RBC/f—Average number of Red Blood Cells per frame (Column RBCs divided by Column 5 ROI).
Column RBC/f (%)—This is the RBC/frame value at a particular sampling percentage divided by the RBC/frame for the 100% sampling case (top line). This is an estimate of the accuracy of the particular sampling percentage compared to counting 100% of the cells.
Column WBC/f—Average number of White Blood Cells per frame (Column WBCs divided by Column ROI).
Column 9 WBC/f (%)—This is similar to Column 7 but estimates the accuracy of the sampling percentage for the White Blood Cells.
Column RBC/WBC—This is the ratio of RBC/WBC for the particular sampling percentage.
Results: A small percentage of the total frames can provide accurate results. As a smaller fraction of the total frames are counted, the accuracy is maintained down to 1% for Red Blood Cells and down to 5% for White Blood Cells.
Discussion: In these experiments, it took approximately one second to capture an image pair. For this experiment, where almost 10,000 image pairs were needed to capture 100% of the sample, this means that image analysis took 10,000 seconds or approximately 2.8 hours. The experiment shows that the uniformity of the distribution of cells across the imaging chamber was good enough to provide accurate results by counting cells in only 5% of the frames. The goal of "counting every cell" is achieved because the entire sample size (the Region of Interest ROI) is measured, but only 5% of the images need to be analyzed to get accurate results. This reduces the image analysis time to approximately 8 minutes. It is expected that advances in camera and computer processing technology will further reduce this time.

The present invention has now been described in connection with a number of specific embodiments thereof. However, numerous modifications which are contemplated as falling within the scope of the present invention should now be apparent to those skilled in the art. Therefore, it is intended that the scope of the present invention be limited only by the scope of the claims appended hereto. In addition, the order of presentation of the claims should not be construed to limit the scope of any particular term in the claims.

What is claimed is:

1. A method of counting and analyzing red cells, white cells, and platelets, utilizing an automated microscope with image processing software, and a single use test cartridge having a single, serpentine imaging chamber, the method comprising:
    a) diluting a known volume of test sample of whole blood with a known volume of diluent and/or stain to obtain a known dilution ratio between 10:1 to 250:1,
    b) mixing the test sample and diluent and/or stain to a substantially uniform mixture,
    c) introducing a portion of the mixture into single the imaging chamber of the test cartridge, the chamber having a shape in planar view which is serpentine, wherein the imaging chamber is defined by walls in the test cartridge and has a bottom and a predetermined depth, wherein the serpentine chamber has dimensions that keep a distribution of cells and platelets in the chamber substantially uniform, at the known dilution ratio, as the cells and platelets in the mixture settle to the bottom of the imaging chamber to form a monolayer wherein the cells and platelets do not crowd or overlap,
    d) introducing the test cartridge with the portion of the mixture into the automated microscope with image processing software,
    e) capturing one or more digital images of the settled red cells, white cells and platelets in the portion of the mixture in the monolayer in the single serpentine imaging chamber that are selected to be statistically representative of a number and distribution of the red cells, white cells, and platelets in the mixture in the imaging chamber, and
    f) deriving a quantitative characterization of the distribution of the red cells, white cells, and platelets in the serpentine imaging chamber based on the images captured of the settled red cells, white cells and platelets in the portion of the mixture.

2. A method of claim 1 wherein the step of deriving a quantitative characterization includes analyzing the red cells, white cells and platelets in the captured images with pattern recognition software.

3. A method of claim 1 wherein the step of deriving a quantitative characterization includes counting all of at least one type of cell in the images using the imaging processing software, and calculating the at least one type of cell per unit volume in the sample.

4. A method of claim 1 wherein the capturing of the one or more digital images includes brightfield and fluorescent images.

5. A method of claim 1 wherein a geometry of the imaging chamber has dimensions that are sufficient that the red cells, white cells and platelets do not overlap, crowd, or screen when they settle to the bottom of the imaging chamber.

6. A method of claim 1 wherein the step of capturing the one or more digital images includes capturing images that include all the red cells, white cells and platelets in the imaging chamber.

7. A method of claim 1 wherein a rate of introducing of the mixture of diluent and sample is such that the portion of the mixture remains substantially uniform.

8. A method of claim 1 wherein the serpentine imaging chamber includes a plurality of convex curves, wherein each of the convex curves has an inside turning diameter and an outside turning diameter, and wherein the outside turning diameter of each of the convex curves is about twice the inside turning diameter of the convex curves of the serpentine imaging chamber.

9. A method of claim 1 wherein the depth of the imaging chamber is uniform throughout a length of the imaging chamber and the depth is between 10 μm and 200 μm.

10. A method of claim 1 wherein a width and the depth of the imaging chamber are uniform throughout a length of the imaging chamber and a depth to width ratio of the imaging chamber is greater than 2 to 1.

11. A method of claim 1 further comprising performing a three-part differential of white cells in the sample.

12. A method of claim 1 further comprising performing a five-part differential of white cells in the sample.

* * * * *